United States Patent [19]

Saccomano et al.

[11] Patent Number: 5,227,397
[45] Date of Patent: Jul. 13, 1993

[54] POLYAMINES AND POLYPEPTIDES USEFUL AS ANTAGONISTS OF EXCITATORY AMINO ACID NEURO-TRANSMITTERS AND/OR AS BLOCKERS OF CALCIUM CHANNELS

[75] Inventors: Nicholas A. Saccomano; Robert A. Volkmann, both of Groton, Conn.

[73] Assignee: Pfizer Inc., New York, N.Y.

[21] Appl. No.: 554,311

[22] Filed: Jul. 17, 1990

Related U.S. Application Data

[63] Continuation-in-part of Ser. No. 491,066, Mar. 14, 1990, abandoned, which is a continuation-in-part of Ser. No. 346,181, Apr. 28, 1989, abandoned.

[51] Int. Cl.$^5$ .................. C07D 209/12; A61K 31/415
[52] U.S. Cl. ..................................... 514/419; 548/495; 514/12
[58] Field of Search ....................... 548/495; 514/419

[56] References Cited

U.S. PATENT DOCUMENTS

| 4,925,664 | 5/1990 | Jackson et al. | 424/537 |
| 4,950,739 | 8/1990 | Cherksey et al. | 530/350 |
| 5,037,846 | 8/1991 | Saccomano et al. | 519/419 |

FOREIGN PATENT DOCUMENTS 8907608 8/1989 PCT Int'l Appl.

OTHER PUBLICATIONS

Wayne S. Skinner, et al., "Purification and Characterization of Two Classes of Neurotoxins from the Funnel Web Spider, *Agelenopsis aperta*", J. Biol. Chem. 264:2150–2155 (1989).

H. Jackson, et al., "Spider toxins as tools for dissecting elements of excitatory amino acid transmission", Trends in Neuroscience 11:278–283 (1988).

B. Cherksey et al., "Isolation of a voltage dependent calcium channel from the squid nervous system", Biophys, J. 55:438a (1989).

V. P. Bindokas, et al., "ω-AGAI, A Spider Venom Toxin from *Agelenopsis aperta*, Irreversibly Blocks Transmitter Release at Insect and Frog Neuromuscular Junctions", Soc. Neuroscience Abstracts 14:30 (No. 17.11) (1988).

M. E. Adams, et al., "Spider Venom Toxins Acting on Three Classes of Synaptic Ion Channels at the Insect Neuromuscular Junction", Soc. Neuroscience Abstracts 14:30 (No. 17.10) (1988).

M. Sugimori, et al., "Spider Venom Blockade of Dendritic Calcium Spiking in Purkinje Cells Studied In Vitro", Soc. Neuroscience Abstracts 13:228 (No. 69.1) (1987).

H. Jackson, et al., "Suppression of Chemically-Induced Behavioral Seizures in Rats by a Novel Spider Toxin", Soc. Neuroscience Abstracts 13:1078 (No. 300.6) (1987).

H. Jackson, et al., "Presynaptic Blockade of Transmission by a Potent, Long-Lasting Toxin from *Agelenopsis aperta* Spiders", Soc. Neuroscience Abstracts 12:730 (No. 197.4) (1986).

*Primary Examiner*—David B. Springer
*Attorney, Agent, or Firm*—Peter C. Richardson; Gregg C. Benson; D. Stuart McFarlin

[57] ABSTRACT

This invention relates to certain polyamines and polypeptides found to be present in the venom of the *Agelenopsis aperta* spider. The polyamines of this invention and the salts thereof antagonize excitatory amino acid neurotransmitters, which neurotransmitters affect cells of various organisms and are useful in antagonizing said neurotransmitters, per se, in the treatment of excitatory amino acid neurotransmitter mediated diseases and conditions and in the control of invertebrate pests. The polypeptides of this invention and one of said polyamines and the salts thereof block calcium channels in cells of various organisms and are useful in blocking said calcium channels in cells, per se, in the treatment of calcium channel mediated diseases and conditions and in the control of invertebrate pests. This invention also relates to compositions comprising said polyamines, polypeptides and salts thereof.

28 Claims, No Drawings

OTHER PUBLICATIONS

L. M. Kerr, et al., "Effects of Spider Toxins and L and N CNS Calcium Channels: Inhibition and Enhancement of Binding", Soc. Neuroscience Abstracts 13:102 (No. 31.15) (1987).

J. Hollis, et al., "Effects of Spider Venom on Vertebrate CNS Glutamate Binding", Soc. Neuroscience Abstracts 13:756 (No. 209.3) (1987).

H. Jackson, et al., "Spider Venoms Block Synaptic Transmission Mediated by Non-N-methyl-D-aspartate Receptors in the Avian Cochlear Nucleus", Soc. Neuroscience Abstracts 11:107 (No. 32.17) (1985).

R. Llinas, et al., "Blocking and isolation of a calcium channel from neurons in mammals and cephalopods utilizing a toxin fraction (FTX) from funnel-web spider poison", PNAS 86:1689-1693 (1989).

Nerotox '88 Molecular Basis of Drug & Pesticide Action, G. G. Lunt, Ed., Excerpta Medica, Amsterdam-New York-Oxford, 1988, Chapter 4, pp. 49-59.

V. P. Bindokas, et al., "ω-Aga-I: A Presynaptic Calcium Channel Antagonist from Venom of the Funnel Web Spider, *Agelenopsis aperta*," J. Neurobiology 20:171-188 (1989).

B. C. Albensi, et al., "Effects of Calcium Antagonist Peptide Spider Toxins on Hippocampal Synaptic Transmission Studied In Vitro," Soc. Neurosci, Abstr., 15:652 (No. 373.11) (1989).

L. D. Artman, et al., "Peptide Toxins from *Agelenopsis aperta* Spider Venom Block Depolarization-Induced Increases in Cytosolic Free Calcium in Rat Cerebellar Granule Neurons", Soc. Neurosci. Abstr. 15:356 (No. 147.17) (1989).

V. P. Bindokas, et al., "Are Two Sub-Types of Presynaptic Calcium Channels Involved in Neurotransmitter Release at the Insect Neuromuscular Junction?" Soc. Neurosci. Abstr. 15:26 (No. 16.6) (1989).

J. M. Pocock, et al., "Effects of ω-Agatoxins on Voltage-Department $Ca^{++}$ Flux in Chick Brain Synaptosomes", Soc. Neurosci. Abstr. 15:652 (No. 264.7) (1989).

M. E. Adams, et al., "ω-Agatoxins: A Family of Neuronal $Ca^{++}$ Channel Antagonists from Funnel Web Spider (*Agelenopsis aperta*) Venom", Soc. Neurosci. Abstr. 15:652 (No. 264.6) (1989).

J. W. Lin, et al., "A Funnel-Web Spider Toxin (FTX) Fraction Blocks Calcium Currents Induced by Rat Brain mRNA in Xenopus Oocytes", Soc. Neurosci. Abstr. 15:652 (No. 264.9) (1989).

T. N. Parks, et al., "Polyamine Spider Toxins Block NMDA Receptor-Mediated Increases in Cytosolic Calcium in Cerebellar Granule Neurons", Soc. Neurosci. Abstr. 15:1169 (No. 463.25) (1989).

M. E. Adams, et al., "ω-Agatoxins: Novel Calcium Channel Antagonists of Two Subtypes from Funnel Web Spider (*Agelenopsis aperta*) Venom", J. Biol. Chem. 265:861-867 (1990).

A. L. Mueller, et al., "Effects of Polyamine Spider Toxins on NMDA Receptor-Mediated Transmission in Rat Hippocampus In Vitro", Soc. Neurosci. Abstr. 15:945 (No. 373.10) (1989).

A. L. Mueller, et al., "Polyamine Spider Toxins as Novel NMDA Receptor Antagonists", Symposium-The Neurobiology of the NMDA Receptor: From Chemistry to Clinic, Pittsburgh, Pa., Oct. 27-28, 1989.

T. Chaudhary, et al., "Use of $^{252}$Cf Plasma Desorption and Laser Desorption MS to Elucidate an Unexpected Modification of a Neurotoxic Protein", 38th ASMS Conference on MS and Allied Topics, Tucson, Ariz., Jun. 3-8, 1990.

H. Jackson, et al., "Effects of Spider Venoms on Transmission Mediated by Non-N-Methyl-D-Aspartate Receptors in the Avian Cochlear Nucleus", Excitatory Amino Acid Transmission, pp. 51-54 (1987).

POLYAMINES AND POLYPEPTIDES USEFUL AS ANTAGONISTS OF EXCITATORY AMINO ACID NEURO-TRANSMITTERS AND/OR AS BLOCKERS OF CALCIUM CHANNELS

CROSS REFERENCE TO RELATED APPLICATION

This is a continuation-in-part of application Ser. No. 07/491,066, filed Mar. 14, 1990, which is a continuation-in-part of application Ser. No. 07/346,181, filed Apr. 28, 1989, both abandoned.

BACKGROUND OF THE INVENTION

1. Field of the Invention

This invention relates to certain polyamines and polypeptides found to be present in the venom of the *Agelenopsis aperta* spider. The polyamines and the pharmaceutically-acceptable salts thereof antagonize excitatory amino acid neurotransmitters, which neurotransmitters affect cells including neuronal cells of a variety of organisms including invertebrates and vertebrates. The polypeptides and one of said polyamines and the pharmaceutically-acceptable salts thereof block calcium channels in cells including neuronal and muscle cells of various organisms including invertebrates and vertebrates. This invention also relates to the use of such polyamines and their salts in antagonizing excitatory amino acid neurotransmitters, which neurotransmitters affect cells such as cells in the nervous system of an organism, per se, in the treatment of excitatory amino acid neurotransmitter mediated diseases and conditions in a mammal and control of invertebrate pests, and to compositions comprising said polyamines and salts thereof. Further, this invention relates to the use of said polypeptides and one of said polyamines and their salts in blocking calcium channels in cells such as cells in the nervous and muscular system of an organism, per se, in the treatment of calcium channel mediated diseases and conditions in a mammal, and in the control of invertebrate pests, and to compositions comprising said polypeptides, polyamine and salts thereof.

2. Background of the Invention

It has been reported that the venom of the spider *Agelenopsis aperta* contains at least two toxins which affect calcium currents. Jackson, H., et al., Soc. Neu. Sci. Abstr. 12:1078 (1987). Those authors disclose a toxin, referred to therein as AG2, which has a molecular weight of less than 1,000 daltons and appears to suppress calcium currents in a broad range of tissues. Further, Jackson, H., et al., Soc. Neu. Sci. Abstr. 12:730 (1986) report another toxin from *Agelenopsis aperta* comprising a component of about 6,000 M.W. That toxin is reported to effect presynaptic blockade of transmission and it has been suggested that the toxin blocks calcium channels associated with the release of neurotransmitter.

Compounds which are excitatory amino acid neurotransmitter antagonists have a variety of utilities. Excitatory amino acid neurotransmitter antagonists can find clinical application in the treatment of such conditions as seizure, stroke, cerebral ischemia, neuronal degeneration disorders such as Alzheimer's disease and epilepsy and as psychotherapeutants, among others. See *Excitatory Amino Acids in Health and Disease*, D. Lodge, Ed., John Wiley and Sons Ltd., New York, N.Y. 1988, the teachings of which are incorporated herein by reference. Further, such compounds are useful in the study of the physiology of cells such as neuronal cells and in the control of invertebrate pests.

Compounds which are calcium antagonists have a variety of utilities. Calcium antagonists can find clinical application in the treatment of such conditions as angina, hypertension, cardiomyopathies, supraventricular arrhythmias, aesophogeal achalasia, premature labor and Raynaud's disease among others. See W. G. Nayler, *Calcium Antagonists*, Academic Press, Harcourt Brace Javanovich Publishers, New York, N.Y. 1988, the teachings of which are incorporated herein by reference. Further, such compounds are useful in the study of the physiology of cells such as neuronal and muscle cells and in the control of invertebrate pests.

SUMMARY OF THE INVENTION

This invention concerns polyamines and polypeptides found to be present in the venom of the *Agelenopsis aperta* spider. The polyamines of this invention and the fractions in which they are present according to this invention are as follows.

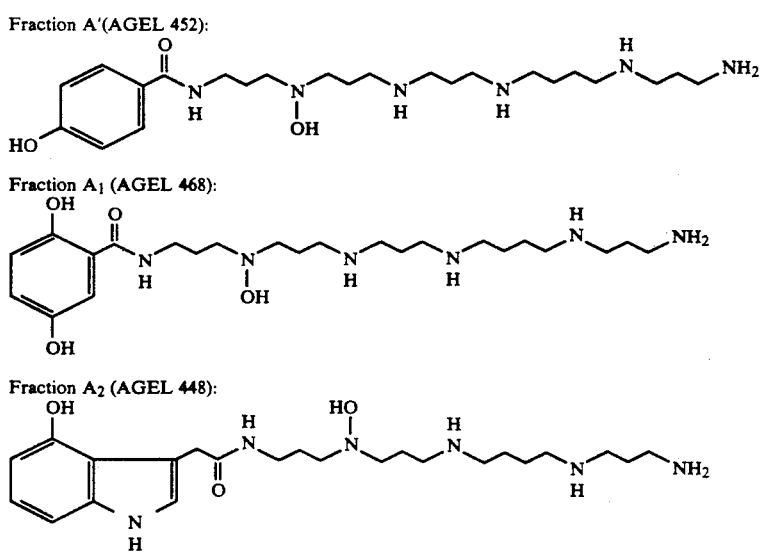

Fraction B₁ (AGEL 505):

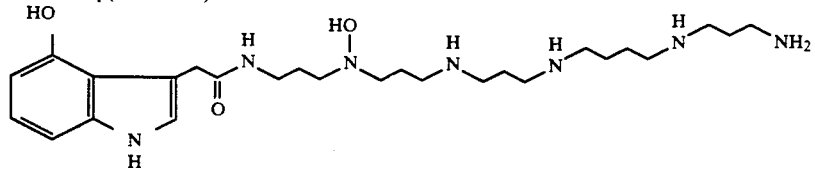

Fraction B₂ (AGEL 505):

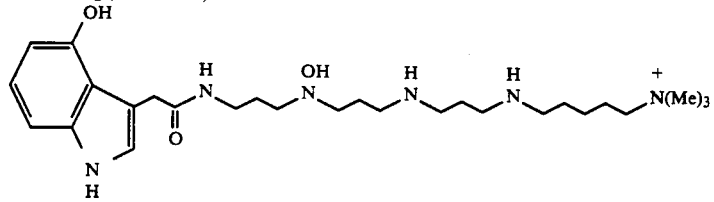

Fraction E (AGEL 489):

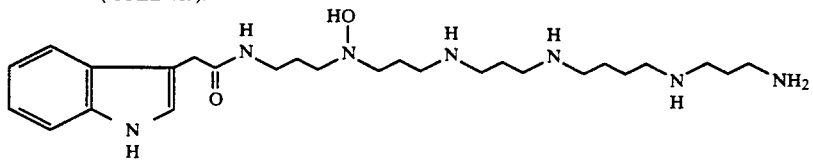

The polypeptides of this invention and the fractions in which they are present according to this invention are as follows.

Fraction G:
H₂N—glu—lys—gly—leu—pro—glu—gly—ala—glu—cys—asp—
gly—asn—glu—ser—asp—cys—lys—cys—ala—gly—gln—trp—
ile—lys—cys—arg—cys—pro—trp—lys—trp—his—ile—thr—
gly—glu—gly—pro—cys—thr—cys—gly—arg—gly—leu—lys—
lys—thr—cys—ile—ser—lys—leu—ser—cys—pro—asn—arg—
               |
              SS—cys—pro—ser—NH₂
asn—glu—trp—COOH; FAB MS: 7267.

Fraction H₁:

H₂N—ala—cys—val—gly—glu—asn—gln—gln—
cys—ala—asp—trp—ala—gly—pro—his—cys—cys—
asp—gly—tyr—tyr—cys—thr—cys—arg—tyr—
phe—pro—lys—cys—ile—cys—arg—asn—
asn—asn—CONH₂; FAB MS: 4198.

Fraction H₂:
H₂N—ala—lys—ala—leu—pro—pro—gly—ser—
val—cys—asp—gly—asn—glu—ser—asp—cys—lys—
cys—tyr—gly—lys—trp—his—lys—cys—
arg—cys—pro—trp—lys—trp—his—phe—thr—
gly—glu—gly—pro—cys—thr—cys—glu—lys—gly—
met—lys—his—thr—cys—ile—thr—lys—leu—his—
               |
              SS—cys—pro—ser—NH₂
cys—pro—asn—lys—ala—glu—trp—gly—leu—asp—trp—COOH;
Ion-Spray MS:7793.

Fraction I:
H₂N—asp—cys—val—gly—glu—ser—gln—gln—
cys—ala—asp—trp—ala—gly—pro—his—cys—cys—
asp—gly—try—tyr—cys—thr—cys—arg—tyr—
phe—pro—lys—cys—ile—cys—val—asn—asn—asn—CONH₂; FAB
MS: 4158.

Fraction J:
H₂N—asp—glu—pro—cys—ile—pro—leu—gly—lys—
ser—cys—ser—trp—lys—ile—gly—thr—pro—tyr—
cys—cys—pro—his—pro—asp—ala—gly—arg—
arg—thr—trp—cys—leu—val—asp—tyr—ser—arg—
phe—val—thr—ile—cys—ser—gly—arg—lys—tyr—CONH₂;
molecular weight for the entire polypeptide
according to FAB MS: 5506.

Fraction L₁:
An amino-terminal amino acid sequence comprising:
H₂N—ile—val—gly—gly—lys—thr—ala—lys—phe—
gly—asp—tyr—pro—trp—met—val—ser—ile—
gln—gln—lys—asn—lys—lys—gly—gly—phe—asp—; approximate molecular weight for the entire polypeptide
of about 20,000.

Fraction L₂:
A polypeptide obtained as described in Example 9.

Fraction M:
An amino-terminal amino acid sequence comprising:
H₂N—glu—ala—thr—glu—ala—ala—lys—val—leu—
ser—asn—leu—asp—glu—thr—val—asp—pro—; approximate
molecular weight for the entire polypeptide of
about 80,000.

The polyamines of this invention and the pharmaceutically-acceptable salts thereof antagonize excitatory amino acid neurotransmitters, which neurotransmitters affect cells. Thus, said polyamines are useful in antagonizing said neurotransmitters, per se. The polyamines of this invention are also useful in the control of invertebrate pests and in the treatment of diseases and conditions in a mammal mediated by excitatory amino acid neurotransmitters. Said polyamines are useful, also, as psychotherapeutants for a mammal.

The polyamine B₁, above, and the polypeptides of this invention block calcium channels in cells. Thus, said polyamine B₁ and polypeptides are useful in blocking calcium channels in cells, per se. Said polyamine B₁ and said polypeptides are also useful in the control of invertebrate pests and in the treatment of diseases and conditions in a mammal mediated by calcium channel function in cells.

Also within the scope of this invention are polypeptides which have substantially the same amino acid sequence and substantially the same calcium channel blocking activity as the polypeptides described above.

This invention also concerns pharmaceutical compositions comprising said polyamines and polypeptides and methods of administering said polyamines and polypeptides.

DETAILED DESCRIPTION OF THE INVENTION

Venom is obtained from the *Agelenopsis aperta* spider through the process of milking by electrical stimulation according to standard methods well known to those skilled in the art. It is preferred that the method employed is one which safeguards against contamination of the whole venom by abdominal regurgitant or hemolymph. Such methods are well known to those skilled in the art. The whole venom so obtained is stored in a frozen state at about −78° C. until used for purification as described below.

Purification of the constituents from the whole venom is accomplished by reverse phase high performance liquid chromatography (HPLC) on a variety of preparative and semi-preparative columns such as C-4 and C-18 Vydac ® columns (Rainin Instrument Co. Inc., Mack Road, Woburn Mass. 01801). Peak detection is carried out monochromatically at 220-230 nm. Further analysis of the fractions can be accomplished with, for example, polychrome UV data collected with a Waters 990 diode array detector (Millipore Corporation, Waters Chromatography Division, 34 Maple Street, Milford, Mass. 01757). The fractions from the columns are collected by known methods such as through the use of an ISCO/"FOXY" fraction collector and an ISCO 2159 peak detector (ISCO, 4700 Superior, Lincoln, Nebr. 68504). The fractions are collected in appropriately sized vessels such as sterile polyethylene laboratory-ware. Concentration of the fractions is then accomplished by lyophilization from the eluant followed by lyophilization from water. Purity of the resulting constituent fractions then can be determined by chromatographic analysis using an analytical column with a gradient system which is more isocratic than the system used in the final purification of the fractions.

The structures comprised by the respective fractions are determined according to known analytical methods such as by mass spectrometry and nuclear magnetic resonance. The polypeptides of this invention are sequenced according to known methods. For example, S-pyridylethylation of cystine residues of the polypeptide under study can be performed in solution followed by amino acid sequencing of the polypeptide. One such procedure for S-pyridylethylation is as follows. About 1 to 10 μg of polypeptide is dissolved or diluted in up to 50 μl of a buffer prepared by mixing 1 part 1M TrisHCl, pH 8.5 containing 4 mM EDTA and 3 parts 8M guanidine·HCl. Then, 2.5 μl of 10% aqueous 2-mercaptoethanol is added and the mixture is incubated at room temperature in the dark under argon for two hours. After incubation, 2 μl of 4-vinylpyridine (fresh reagent stored under argon at −20° C.) is added and the mixture is incubated for another two hours at room temperature in the dark under argon. The mixture is then desalted, preferably by chromatography on a short, reverse phase column. The recovered alkylated polypeptide is then sequenced according to known methods.

In practicing this invention and employing the general procedure outlined above, it has been found that a suitable column for initial fractionation of the venom is a C-18 Vydac ® 22 mm×250 mm, 300 Å pore size, 10μ particle size column. That column is eluted at a flow rate of 15 ml/min. using a linear gradient program of 95%→80% A, 5%→20% B [0→30 min.] then 80%→30% A, 20%→70% B [30→55 min.] where A is 0.1% aqueous trifluoroacetic acid (TFA) and B is acetonitrile. The fractions are collected as described above. Ten fractions so obtained, labeled A, B, E, G, H, I, J, K, L and M, were chosen for further analysis and/or purification. Additionally, it has been found that fractionation of the whole venom using a C-18 Vydac ® 22 mm×250 mm, 300 Å pore size, 10μ particle size column which is eluted at a flow rate of 15 ml/min. using a linear gradient program of 5%→10% B, 95%→90% A [0→30 min.]where A and B are as described above yields, inter alia, a fraction labelled A' herein. The elution times of the fractions are given below in Examples 1 and 2.

Fractions A, B, G, H, I/J and L are subjected to further purification using a variety of columns and gradient programs. The specifics for each subfractionation and the results thereof are given in Examples 3, 4, 6, 7, 8 and 10 below.

As shown in the following Examples, Fractions A', $A_1$, $A_2$, $B_1$, $B_2$ and E comprise polyamine compounds. Those compounds and the fractions in which they are found are as follows.

Fraction A'(AGEL 452):

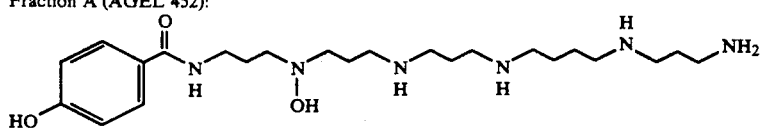

Fraction $A_1$ (AGEL 468):

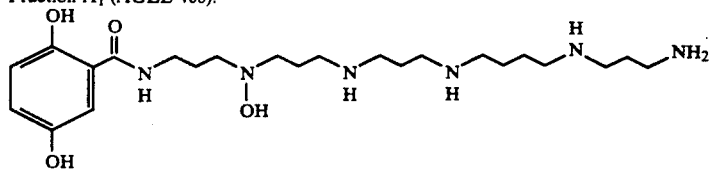

Fraction $A_2$ (AGEL 448):

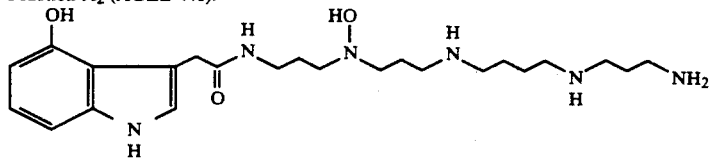

Fraction B₁ (AGEL 505):

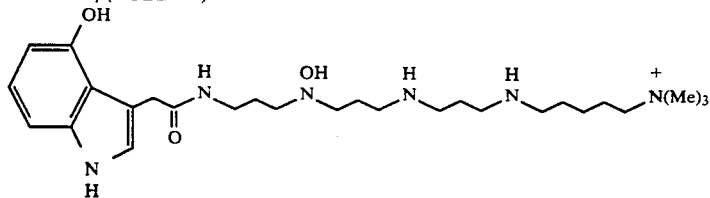

Fraction B₂ (AGEL 505):

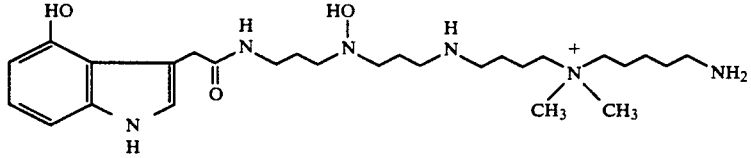

Fraction E (AGEL 489):

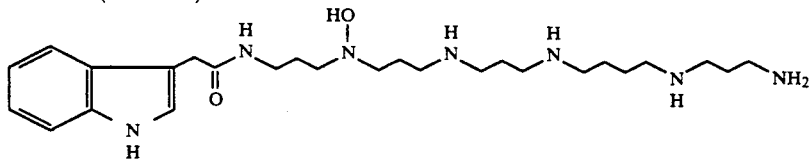

As shown in the following Examples, Fractions G, H₁, H₂, I, J, K, L₁, L₂ and M comprise polypeptides. Those polypeptides and the fractions in which they are found are as follows:

Fraction G:
An amino-terminal amino acid sequence comprising:
H₂N—glu—lys—gly—leu—pro—glu—gly—ala—glu—cys—asp—
gly—asn—glu—ser—asp—cys—lys—cys—ala—gly—gln—trp—
ile—lys—cys—arg—cys—pro—trp—lys—trp—his—ile—thr
gly—glu—gly—pro—cys—thr—cys—glu—arg—gly—leu—lys—
lys—thr—cys—ile—ser—lys—leu—ser—cys—pro—asn—arg
              |
              SS—cys—pro—ser—NH₂
asn—glu—trp—COOH; FAB MS: 7267.

Fraction H₁:
H₂N—ala—cys—val—gly—glu—asn—gln—gln—
cys—ala—asp—trp—ala—gly—pro—his—cys—cys—
asp—gly—tyr—tyr—cys—thr—cys—arg—tyr—
phe—pro—lys—cys—ile—cys—arg—asn—
asn—asn—CONH₂; FAB MS: 4198.

Fraction H₂:
H₂N—ala—lys—ala—leu—pro—pro—gly—ser—
val—cys—asp—gly—asn—glu—ser—asp—cys—lys—
cys—tyr—gly—lys—trp—his—lys—cys—
arg—cys—pro—trp—lys—trp—his—phe—thr—
gly—glu—gly—pro—cys—thr—cys—glu—lys—gly—
met—lys—his—thr—cys—ile—thr—lys—leu—his—
              |
              SS—cys—pro—ser—NH₂
cys—pro—asn—lys—ala—glu—trp—gly—leu—asp—trp—COOH;
Ion-Spray MS:7793.

Fraction I:
H₂N—asp—cys—val—gly—glu—ser—gln—gln—
cys—ala—asp—trp—ala—gly—pro—his—cys—cys—
asp—gly—try—tyr—cys—thr—cys—arg—tyr—
phe—pro—lys—cys—ile—cys—val—asn—asn—asn—CONH₂; FAB MS: 4158.

Fraction J:
H₂N—asp—glu—pro—cys—ile—pro—leu—gly—lys—
ser—cys—ser—trp—lys—ile—gly—thr—pro—tyr—
cys—cys—pro—his—pro—asp—asp—ala—gly—arg—
arg—thr—trp—cys—leu—val—asp—tyr—ser—arg—
phe—val—thr—ile—cys—ser—gly—arg—lys—tyr—CONH₂;
FAB MS: 5506.

Fraction L₁:
An amino-terminal amino acid sequence comprising:
H₂N—ile—val—gly—gly—lys—thr—ala—lys—phe—
gly—asp—tyr—pro—trp—met—val—ser—ile—
gln—gln—lys—asn—lys—lys—gly—gly—phe—asp—; and an approximate molecular weight for the entire polypeptide of about 20,000.

Fraction L₂:
A polypeptide obtained as described in Example 9.

Fraction M:
An amino-terminal amino acid sequence comprising:
H₂N—glu—ala—thr—glu—ala—ala—lys—val—leu—
ser—asn—leu—asp—glu—thr—val—asp—pro—; and an approximate molecular weight for the entire polypeptide of about 80,000.

Given the benefit of the disclosure herein with respect to the compounds present in the fractions of from *Agelenopsis aperta*, it is now possible to obtain said compounds by methods other than through isolation/purification from whole venom. All such methods are within the scope of this invention. For example, the polyamines which are comprised by fractions A', A₁, A₂, B₁, B₂ and E can be made directly by synthetic methods. The polypeptides which are comprised by fractions G, H₁, H₂, I, J, K, L₁, L₂ and M and for which the entire amino acid sequence is described can be produced synthetically by in vitro protein synthesis according to well known methods. For example, such polypeptides can be synthesized using an ABI 430A solid phase peptide synthesizer (Applied Biosystems, Inc., 850 Lincoln Center Drive, Foster City, Calif. 94404) employing standard Merrifield chemistry or other solid phase chemistries well known to those skilled in the art. The polypeptides can also be produced using recombinant DNA techniques through the cloning of coding sequences for the polypeptides or portions thereof. Those polypeptides for which only part of the amino acid sequence is known can be cloned, for example, through the use of hybridization probes which take advantage of the now known amino acid sequence information. A combination of recombinant DNA techniques and in vitro protein synthesis can also be employed to produce the polypeptides of this invention.

It is well known in the art that certain amino acid substitutions can be made in polypeptides which do not affect, or do not substantially affect, the function of said polypeptides. The exact substitutions which are possible vary from polypeptide to polypeptide. Determination of permissible substitutions is accomplished according to procedures well known to those skilled in the art. Thus, all polypeptides having substantially the same amino acid sequence and substantially the same calcium channel blocking activity are within the scope of this invention.

A synthetic scheme for production of certain polyamines of this invention of the formula

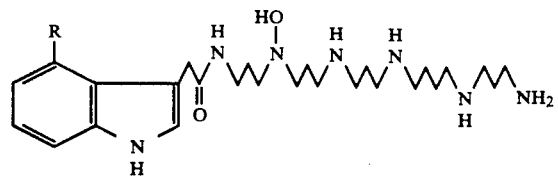

wherein R is H or OH is shown in Reaction Schemes A to D, below.

REACTION SCHEME A

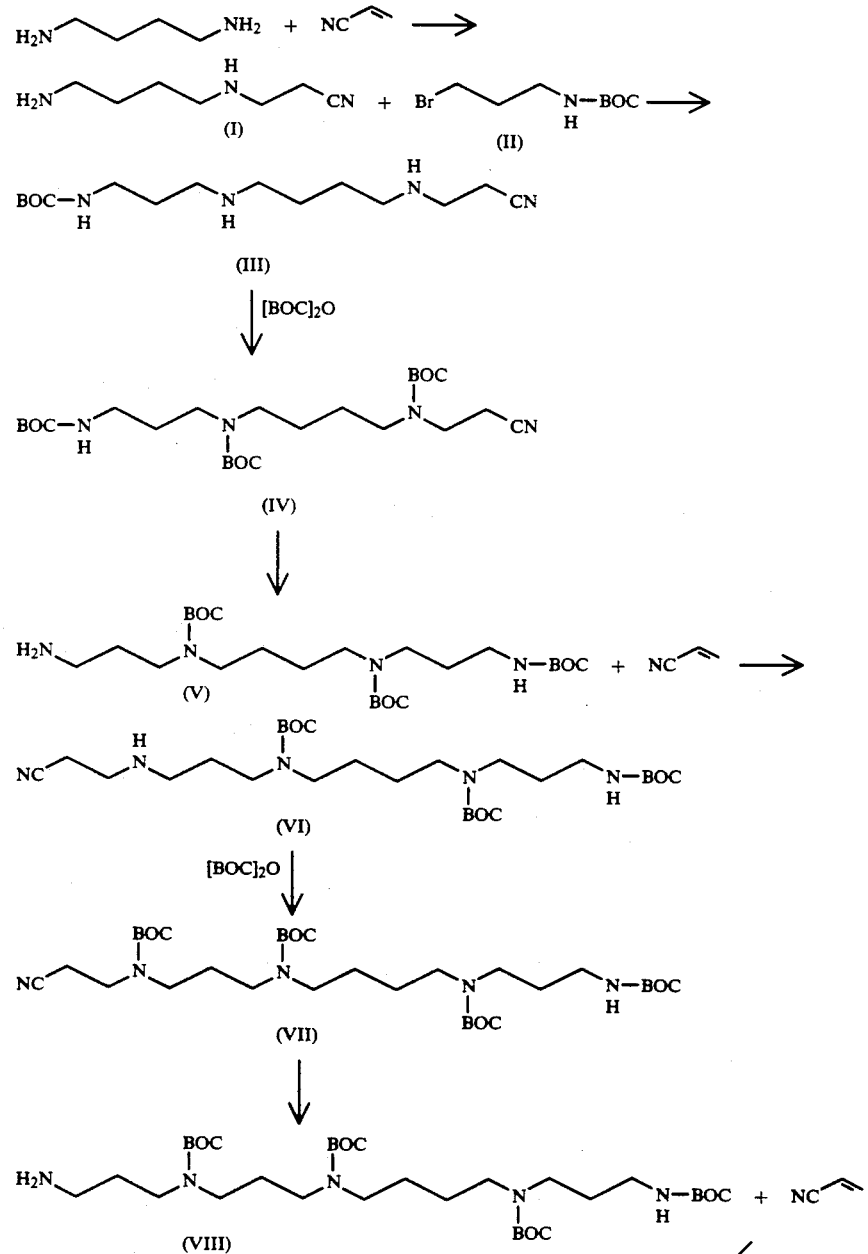

REACTION SCHEME A
-continued
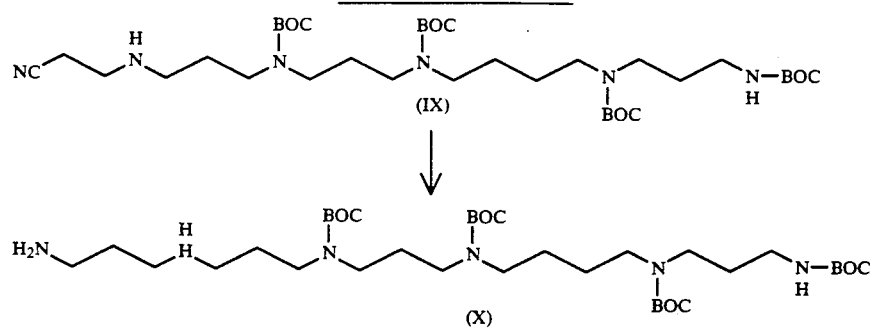
REACTION SCHEME B
-continued REACTION SCHEME B
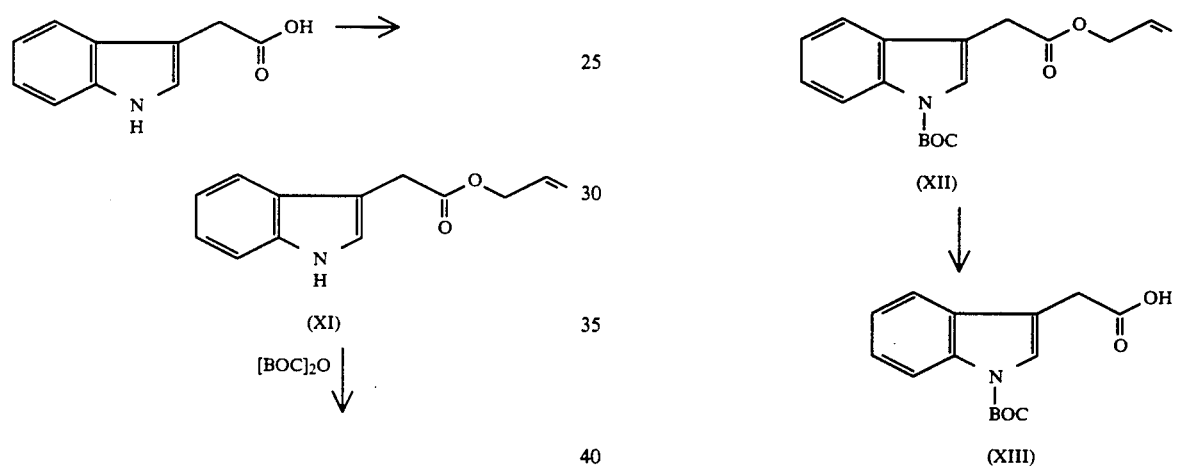
REACTION SCHEME C
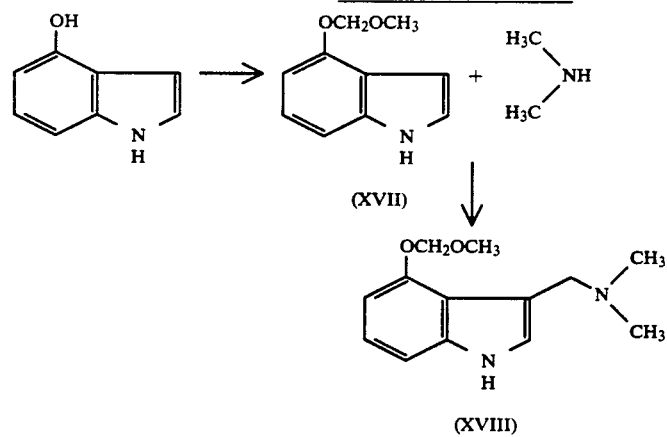
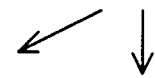

-continued
REACTION SCHEME C
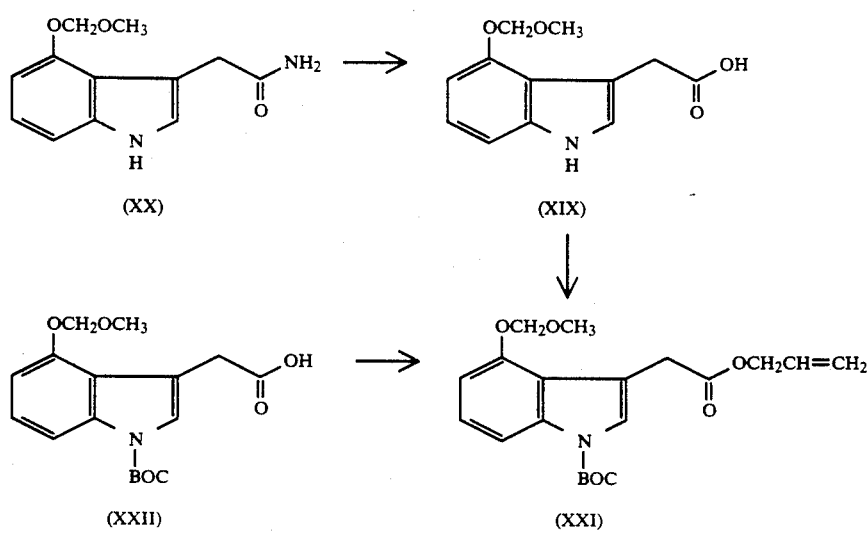
REACTION SCHEME D
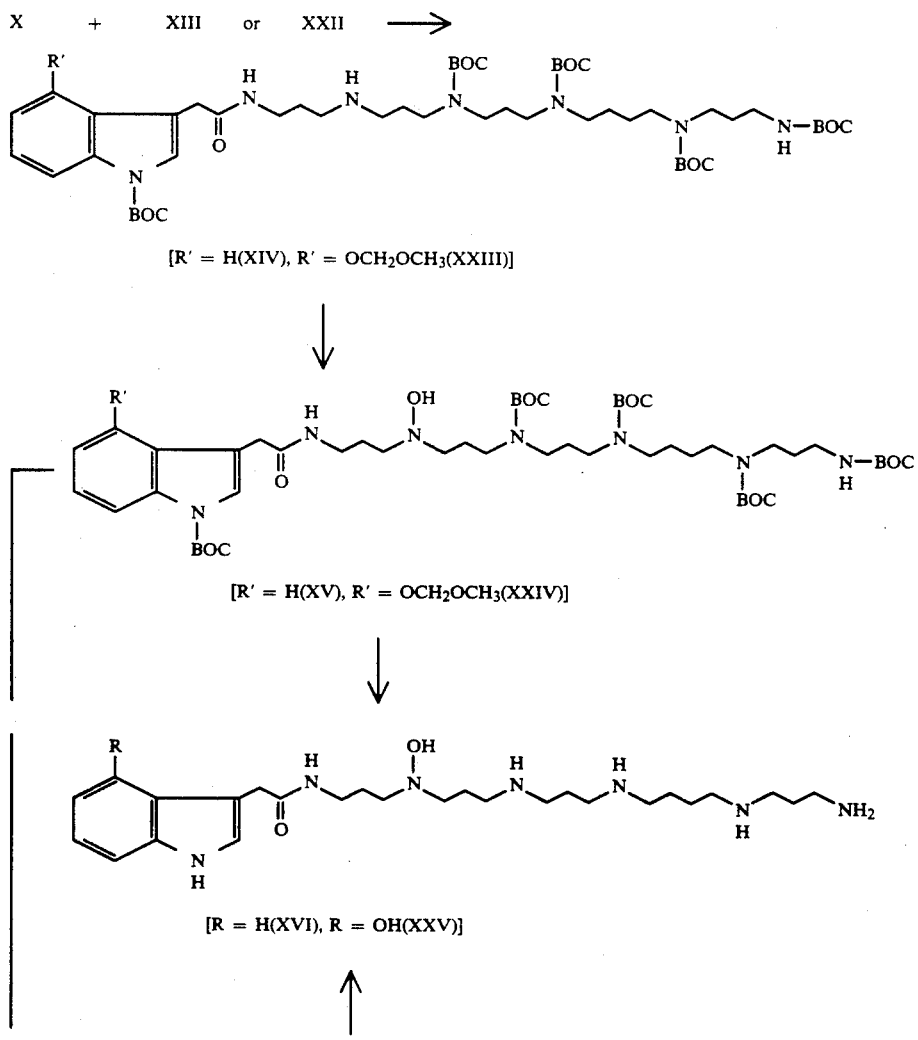

-continued
REACTION SCHEME D
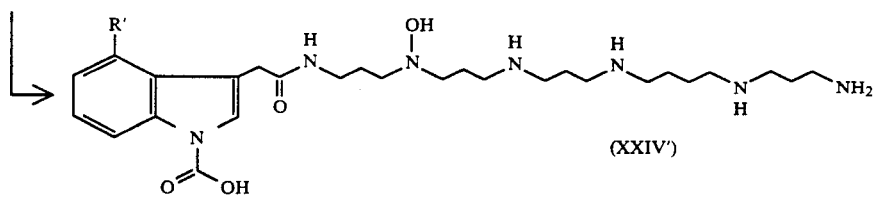
REACTION SCHEME E
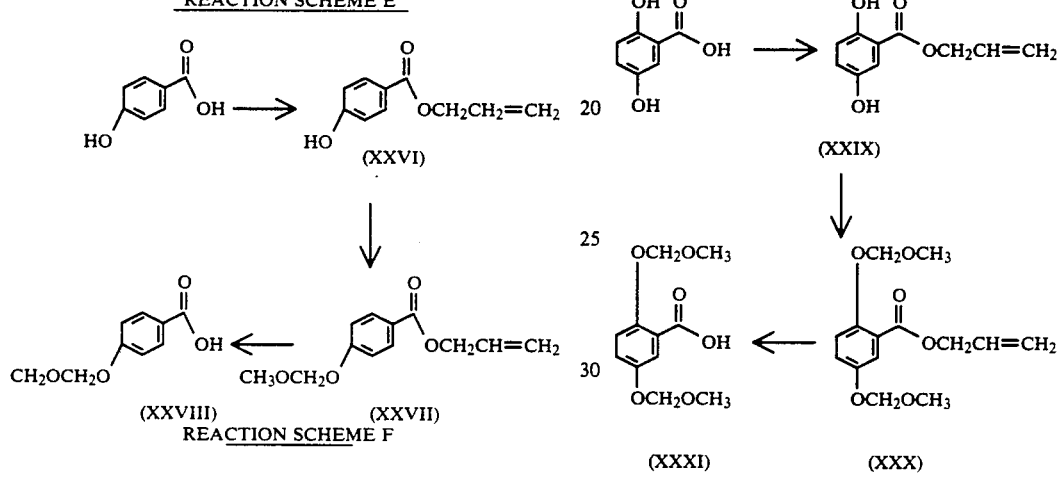
REACTION SCHEME F
REACTION SCHEME G
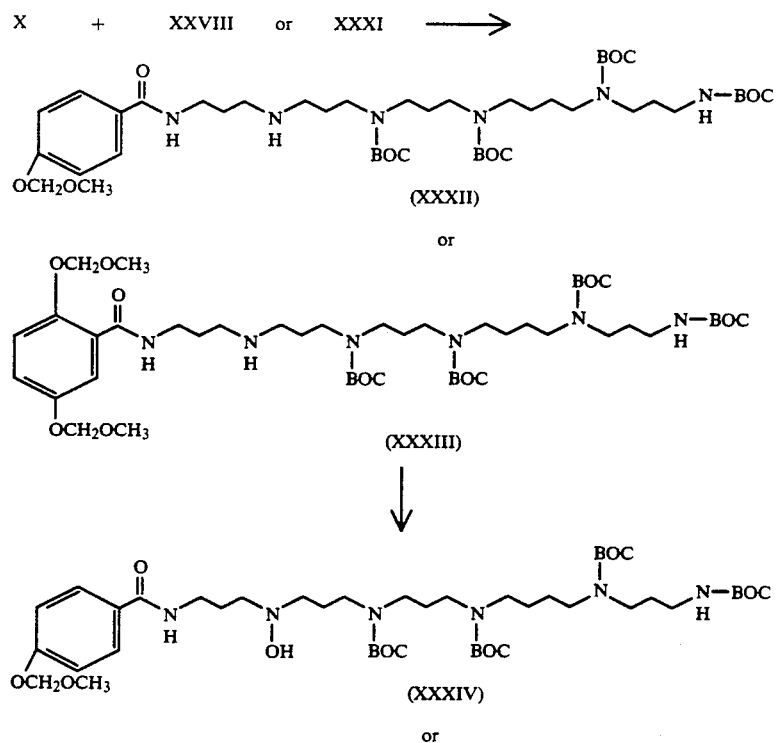

-continued
REACTION SCHEME G
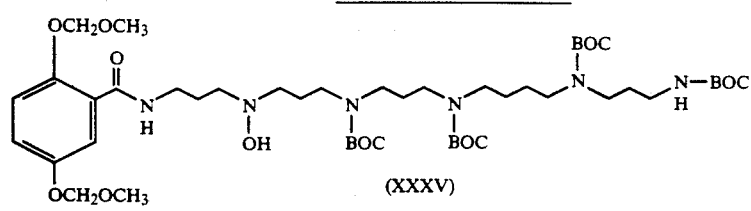
(XXXV)
↓
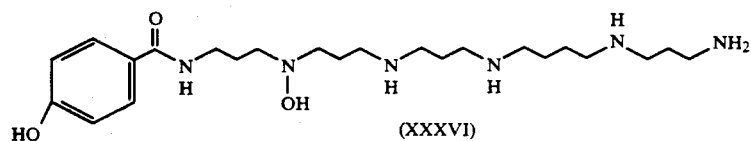
(XXXVI)
or
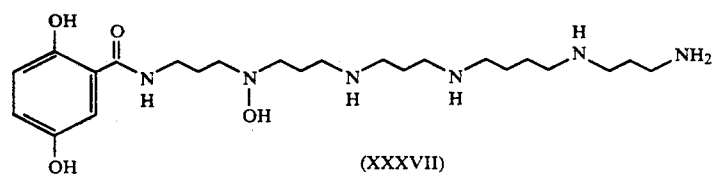
(XXXVII)
REACTION SCHEME H
VI → 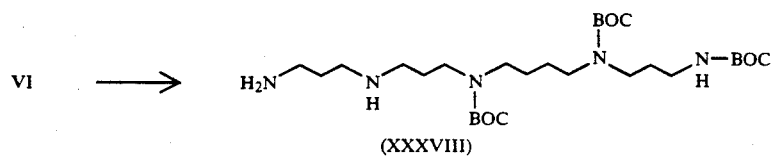
(XXXVIII)
XXXVIII + XXII →
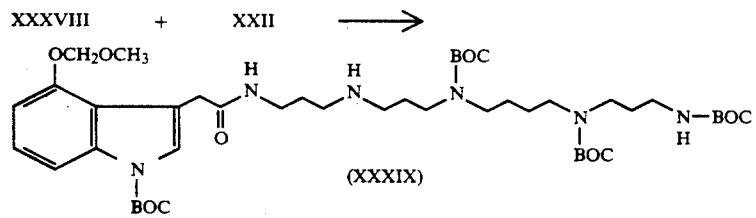
(XXXIX)
↓
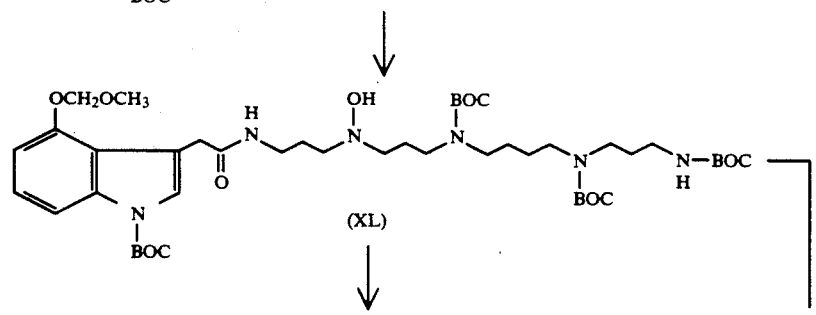
(XL)
↓
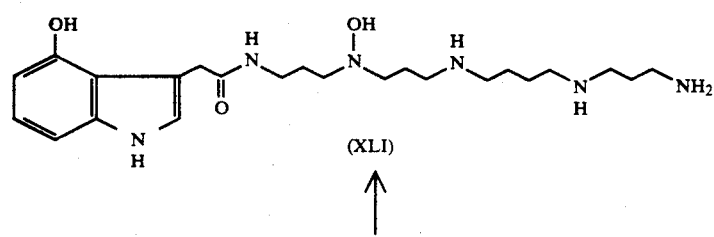
(XLI)
↑

REACTION SCHEME H -continued

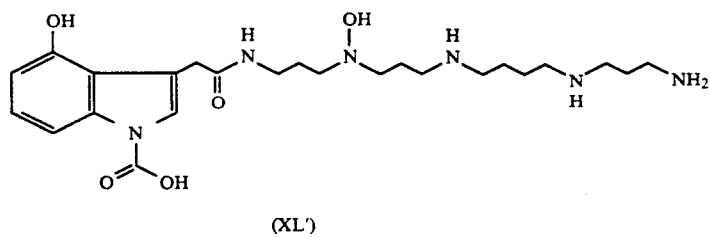

(XL')

According to Reaction Scheme A, the polyamine intermediate compound of formula X is prepared through a sequence of steps beginning with diaminobutane. Reaction conditions suitable to prepare the intermediate compound of formula X according to Reaction Scheme A are given in Example 12, parts A to I. Reaction Scheme B illustrates a method for the preparation of the intermediate compound of formula XIII. Reaction conditions suitable to prepare that intermediate according to Reaction Scheme B are given in Example 12, parts J to L. Preparation of the intermediate compound of formula XXI is shown in Reaction Scheme C. Reaction conditions suitable for the preparation of the compound of formula XXI according to Reaction Scheme C are given in Example 13, parts A to F. Preparation of the polyamine compounds of this invention of the formulae XVI and XXV is shown in Reaction Scheme D. Reaction conditions suitable for the coupling of the intermediate compounds of formulae X and XIII or X and XXI and the subsequent preparation of compounds of the formulae XVI and XXV are given in Example 12, parts M to O and Example 13, parts G to I.

Reaction Schema E and F illustrate methods for the preparation of the intermediate compounds XXVIII and XXXI, respectively. Reaction conditions suitable to prepare the intermediate according to Reaction Scheme E are given in Example 14, parts A to C. Reaction conditions suitable for the preparation of the intermediate according to Reaction Scheme F are given in Example 15, parts A to C. Preparation of the polyamine compounds of this invention of the formulae XXXVI and XXXVII is shown in Reaction Scheme G. Reaction conditions suitable for the coupling of the intermediate compounds of formula X and XXVIII or X and XXXI and the subsequent preparation of compounds of the formulae XXXVI and XXXVII are given in Example 14, parts D to F and Example 15, parts D to F, respectively.

Reaction Scheme H illustrates a method for the preparation of the polyamine compound of this invention of the formula XLI. Reaction conditions suitable for the preparation of the intermediate compound of formula XXXVIII, the coupling thereof to the intermediate compound of formula XXII and the subsequent preparation of the polyamine compound of this invention of the formula XLI are shown in Example 16.

The polyamines of this invention reversibly antagonize excitatory amino acid neurotransmitters, which neurotransmitters affect cells such as cells in the nervous system of a variety of organisms including invertebrates and vertebrates. The term vertebrates as used throughout is meant to include mammals. The term invertebrates as used throughout is meant to include, for example, insects, ectoparasites and endoparasites. The polyamine of fraction $B_1$, as described above, also reversibly blocks calcium channels present in a variety of cells such as cells in the nervous and muscular, including cardiovascular, system of invertebrates and vertebrates.

The ability of the polyamines of the present invention to antagonize excitatory amino acid neurotransmitters is demonstrated by their ability to block N-methyl-D-aspartic acid-induced (NMDA) elevations of cGMP in neonatal rat cerebellums according to the following procedure. Cerebellums from ten 8-14 day old Wistar rats are quickly excised and placed in 4° C. Krebs/bicarbonate buffer, pH 7.4 and then chopped in 0.5 mm × 0.5 mm sections using a McIlwain tissue chopper (The Nickle Laboratory Engineering Co., Gomshall, Surrey, England). The resulting pieces of cerebellum are transferred to 100 ml of Krebs/bicarbonate buffer at 37° C. which is continuously equilibrated with 95:5 $O_2/CO_2$. The pieces of cerebellum are incubated in such a manner for ninety minutes with three changes of the buffer. The buffer then is decanted, the tissue centrifuged (1 min., 3200 r.p.m.) and the tissue resuspended in 20 ml of the Krebs/bicarbonate buffer. Then, 250 µl aliquots (approximately 2 mg) are removed and placed in 1.5 ml microfuge tubes. To those tubes are added 10 µl of the compound under study from a stock solution followed by 10 µl of a 2.5 mM solution of NMDA to start the reaction. The final NMDA concentration is 100 µM. Controls do not have NMDA added. The tubes are incubated for one minute at 37° C. in a shaking water bath and then 750 µl of a 50 mM Tris-Cl, 5mM EDTA solution is added to stop the reaction. The tubes are placed immediately in a boiling water bath for five minutes. The contents of each tube then are sonicated for 15 seconds using a probe sonicator set at power level three. Ten microliters are removed and the protein determined by the method of Lowry, Anal. Biochem. 100:201-220 (1979). The tubes are then centrifuged (5 min., 10,000 xg), 100 µl of the supernatant is removed and the level of cyclic GMP (cGMP) is assayed using a New England Nuclear (Boston, Mass.) cGMP RIA assay according to the method of the supplier. The data is reported as pmole cGMP generated per mg. protein.

The polypeptides of this invention irreversibly block calcium channels present in a variety of cells such as cells in the nervous and muscular system of invertebrates and vertebrates.

The ability of the polyamine of Fraction $B_1$ and the polypeptides of Fractions G, $H_1$, $H_2$, I, J, K, $L_1$, $L_2$ and M to block calcium channels is demonstrated by the following procedure. Dissociated rat neocortical neurons are suspended in Krebs bicarbonate buffer, pH 7.4 containing 2mM $CaCl_2$ and 1% boving serum albumin (BSA). The neurons are sedimented by centrifugation and resuspended in the same buffer which additionally contains 1 μM fura2/AM (Sigma Chem. Co., P.O. Box 14508, St. Louis, Mo. 63178). The cells are incubated for 15 minutes at 37° C., washed and then incubated for another 15 minutes in the same buffer without fura2-/AM. The cells are then washed in the above buffer now containing 1.5 mM $CaCl_2$ and equilibrated at room temperature as a concentrated cell suspension for about 5 to 10 minutes. To a quartz cuvette is added 1.2 ml of prewarmed (37° C.) BSA-free buffer containing 1.5 mM $CaCl_2$ and 10 mM glucose, then 0.3 ml of the concentrated cell suspension prepared above. The cuvette is placed in a thermostated (37° C.) holder equipped with a magnetic stirrer and the fluorescence is measured with a fluorescence spectrophotometer such as a Perkin Elmer 650-40 (Perkin Elmer, Wilton, Conn. 06897). The fluorescence signal is allowed to stabilize for about one minute. Then 1–4 μl of a stock solution of the compound under study in Krebs bicarbonate buffer at appropriate concentrations is added to the cuvette. Calibration of the fluorescent signals and fura-2 leakage correction are performed using the established procedures of Nemeth, et al., J. Biol. Chem. 262:5188 (1987). At the completion of each test, the maximum fluorescence value (Fmax) is determined by addition of ionomycin and the minimum fluorescence value (Fmin) is determined by the subsequent addition of 5 mM EGTA to chelate calcium. Employing the foregoing procedure, calcium channel blocking by a subject compound is shown to occur by a decrease in fluorescence upon addition of the subject compound.

Also within the scope of this invention are polypeptides having substantially the same amino acid sequence as the polypeptides of fractions G, $H_1$, $H_2$, I, J, K, $L_1$, $L_2$ and M and which have substantially the same calcium channel blocking activity as said polypeptides.

The polyamines of this invention are useful in antagonizing excitatory amino acid neurotransmitters, per se. As such, the polyamines are also useful in the control of invertebrate pests and in the treatment of excitatory amino acid neurotransmitter-mediated diseases and conditions in a mammal such as seizure, stroke, cerebral ischemia, neuronal degenerative disorders such as Alzheimer's disease and epilepsy. Said polyamines also are useful as psychotherapeutants in a mammal. Further, the polyamines are useful in the study of the physiology of cells including, but not limited to, cells of the nervous system.

The polyamine of Fraction $B_1$ and the polypeptides of this invention are useful as calcium channel blockers in cells, per se. As such, these compounds are also useful in the control of invertebrate pests and in the treatment of diseases and conditions mediated by calcium channels function in cells in a mammal such as angina, hypertension, cardiomyopathies, supraventricular arrhythmias, aesophogeal achalasia, premature labor and Raynaud's disease. Further, these compounds are useful in the study of the physiology of cells including, but not limited to, cells of the nervous and muscular system.

Also within the scope of this invention are the pharmaceutically-acceptable salts of the polyamines and polypeptides of this invention. Such salts are formed by methods well known to those skilled in the art. For example, acid addition salts of the polyamines and base salts of the polypeptides can be prepared according to conventional methods. Acid addition salts of the polyamines such as hydrochloric and trifluoroacetic acid addition salts thereof are preferred. Hydrochloric acid addition salts of the polyamines are particularly preferred.

When a polyamine or polypeptide of this invention is to be administered to a mammal, it can be administered alone or in combination with pharmaceutically-acceptable carriers or diluents in a pharmaceutical composition according to standard pharmaceutical practice. The polyamines and polypeptides can be adminstered orally or parenterally with the parenteral route of administration being preferred for the polypeptides. Parenteral administration includes intravenous, intramuscular, intraperitoneal, subcutaneous and topical administration.

For oral use of a polyamine or polypeptide of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a polyamine or polypeptide or salt thereof of this invention is used in a human subject, the daily dosage will normally be determined by the prescribing physician. However, suitable dosages for the polyamines of this invention are from about 3 to 30 mg/kg/day and suitable dosages of the polypeptides of this invention are those which will result in in vivo concentrations of from about 20 to 500 nM. Moreover, the dosage will vary according to the age, weight and response of the individual patient, as well as the severity of the patient's symptoms and the potency of the particular compound being administered. Therefore, dosages outside the ranges given above are possible and are within the scope of this invention.

When a polyamine or polypeptide or salt thereof of this invention is used in control of invertebrate pests, said compound is administered to said invertebrate directly or provided to the environment of said invertebrate. For example, a compound of this invention can be sprayed as a solution onto said invertebrate. The amount of compound necessary for control of said invertebrate will vary according to the invertebrate and environmental conditions and will be determined by the person applying the compound.

When a polyamine or polypeptide or salt thereof of this invention is used in the physiological study of cells, said compound is administered to the cells according to methods well known to those skilled in the art. For example, said compound can be administered to cells in an appropriate physiological buffer. An appropriate concentration of the compounds of this invention for use in such studies is 100 μM. However, the concentration of said compounds in such studies may be greater than or much less than 100 μM. The amount of the compound administered will be determined by the person skilled in the art according to well known methods.

EXAMPLE 1

Initial fractionation of whole venom of *Agelenopsis aperta*

Whole venom of *Agelenopsis aperta*, obtained from Natural Product Sciences Inc., Salt Lake City, Utah 84108 and which had been stored in the frozen state at about −78° C., was thawed and 10 to 60 μl amounts thereof, diluted to 200 μl, and loaded onto a C-18 Vydac ® (22 mm×250 mm, 300 Å pore size, 10μ particle size) column and eluted using a flow rate of 15 ml/min. and a solvent system using a linear gradient program of 5%→20% B, 95%→80% A [0→30 min.] then 20%→70% B, 80%→30% A [30→55 min.] where A is 0.1% aqueous TFA and B is acetonitrile. Peak detection was carried out monochromatically at 220–230 nm and fractions were collected with an ISCO/"FOXY" fraction collector and an ISCO 2159 peak detector. Fractions were collected from 20 minutes to 60 minutes. Based upon peak detection, the following fractions were collected:

| Fraction | Elution Time |
| --- | --- |
| A | about 21 minutes |
| B | about 22.75 minutes |
| E | about 27.5 minutes |
| G | about 38 minutes |
| H | about 39 minutes |
| I | about 40 minutes |
| J | about 40 minutes |
| K | about 42 minutes |
| L | about 43 minutes |
| M | about 48.3 minutes |

EXAMPLE 2

Fractionation of whole venom of *Agelenopsis aperta* to obtain Fraction A'

Whole venom of *Agelenopsis aperta* was obtained and loaded onto a C-18 Vydac ® column as described in Example 1. The column was eluted using a flow rate of 50 ml/min. and a solvent system using a linear gradient program of 5%→10% B, 95%→90% A [0→30 min.] where A is 0.1% aqueous TFA and B is acetonitrile. Peak detection and fraction collection were performed as described in Example 1. Fraction A' which eluted at about 12.5 minutes was obtained. Fraction A' was then prepared for spectral analysis by lyophilization from the eluent followed by lyophilization from distilled water, according to standard methods.

The structure of the compound which is comprised by fraction A' was then determined by the use of FAB MS. The data so obtained and the structure deduced therefrom are as follows:

A': FAB MS: M/Z 453 (M+1)
Structure: Benzamide, N-(20-amino-4-hydroxy-4,8,12,17-tetraazeicos-1-yl)-4-hydroxy

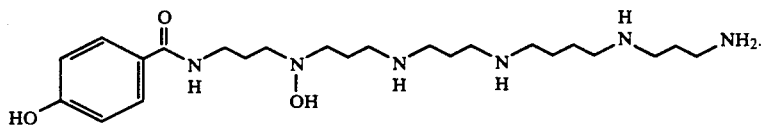

EXAMPLE 3

Subfractionation of Fraction A and Determination of Structures Therein

Fraction A, obtained as described in Example 1, was loaded onto a C-4 Vydac ® (10 mm×250 mm, 300 Å pore size, 5μ particle size) column and eluted therefrom using a flow rate of 4.0 ml/min. and a solvent system using a linear gradient program of 0%→10% B, 100%→90% A [0→30 min.] where A is 0.1% aqueous TFA and B is acetonitrile. Peak detection was accomplished using a Waters 990 diode array detector and fraction collection was accomplished as described in Example 1. Two fractions were obtained as follows:

| Fraction | Elution Time |
| --- | --- |
| $A_1$ | about 7 minutes |
| $A_2$ | about 9 minutes |

Fractions $A_1$ and $A_2$ were then prepared for spectral analysis by lyophilization from the eluent followed by lyophilization from water, according to standard methods.

The structure of the compounds which are comprised by fractions $A_1$ and $A_2$ were then determined by the use of FAB MS. The data so obtained and structures deduced therefrom are as follows:

$A_1$:
FAB MS:M/Z 469 (M+1), high resolution: 469.3863 calc. for $C_{23}H_{45}N_6O$ with 2.0 mmμ error
structure: benzamide, N-(20-amino-4-hydroxy-4,8,12,17-tetraazeicos-1-yl)-2,5-dihydroxy

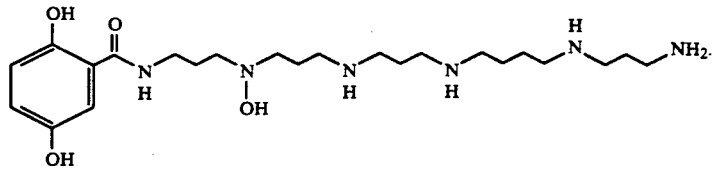

$A_2$:
FAB MS:M/Z 449 (M+1), 433, 376, 260, 203 Structure: 1H-indole-3-acetamide, N-(16-amino-4-hydroxy-4,8,13-triazahexadec-1-yl)-4-hydroxy

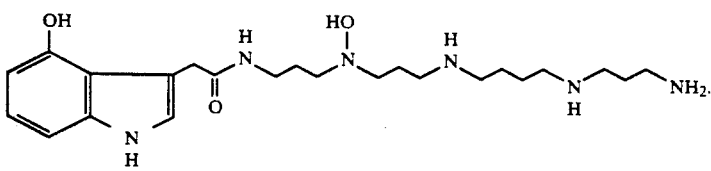

EXAMPLE 4

Subfractionation of Fraction B and Determination of Structures Therein

Fraction B, obtained as described in Example 1, was loaded onto a C-4 Vydac ® (22 mm×250 mm, 300 Å pore size, 10μ particle size) column and eluted off using a flow rate of 15 ml/min. and a solvent system using a non-linear gradient program of 0%→0% B, 100%→100% A [0→5 min.], then 0%→10% B, 100%→90% A [5→20 min.] (Waters curve 1) then 10%→20% B, 90%→80% A [20→0 min.] (Waters curve 6) then 20%→50% B, 80%→50% A [30→40 min.] (Waters curve 11) where A is 0.1% aqueous TFA and B is acetonitrile. Peak detection was accomplished using a Waters 990 diode array detector and fraction collection was accomplished as described in Example 1. Two fractions were obtained as follows:

| Fraction | Elution Time |
|---|---|
| B₁ | about 18.5 minutes |
| B₂ | about 21.5 minutes |

The fractions were then prepared for spectral analysis by lyophilization from the eluent followed by lyophilization from water according to standard methods.

The structure of the compound which is comprised by fraction B₁ was determined by the use of FAB MS and the results thereof are as follows:

FAB MS:M/Z 506 (M+1), 489, 461, 433, 378, 333, 260, 231, 215, 203, 155, 119 high resolution: 506.3810 calc. for $C_{26}H_{48}N_7O_3$ Structure: 1H-indole-3-acetamide, N-(20-amino-4-hydroxy-4,8,12,17-tetraazeicos-1-yl)-4-hydroxy

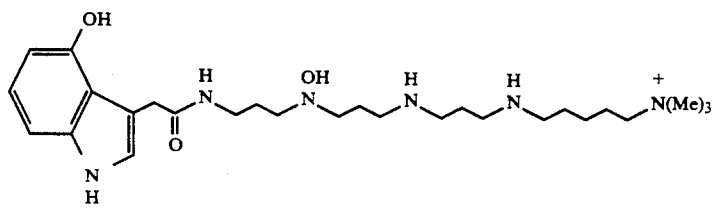

The structure of the compound which is comprised by fraction B₂ was determined by the use of FAB MS and the results thereof are as follows:

FAB MS:
high resolution: 505.3861 calc. for $C_{27}H_{48}N_6O_3$
Structure: 1H-indole-3-acetamide, N-(17-trimethylamino-4-hydroxy-4,8,12-triazaheptadec-1-yl)-4-hydroxy

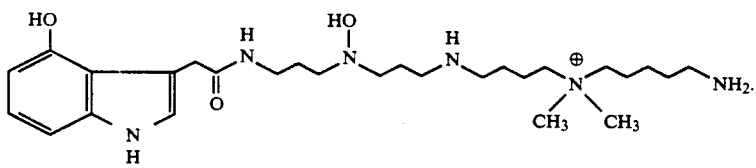

EXAMPLE 5

Structure of Compound Comprised by Fraction E

Fraction E, obtained as described in Example 1, was prepared for spectral analysis by lyophilization from the eluent followed by lyophilization from water according to standard methods. The structure of the compound comprised by fraction E was determined using FAB MS, ¹H-NMR and ¹³C-NMR. The data so obtained and the structure deduced therefrom are as follows:

FAB MS:M/Z 490 (M+1), 472, 433, 362, 333, 260, 215, 203, 177, 155, 119 high resolution: 490.3860 calc. for $C_{26}H_{48}N_7O_2$ with 0.6 mmμ error ¹H-NMR (500 Mhz, d6-DMSO): 10.89 (s, 1H), 8.90-7.85 (m, 6H), 7.55 (d, J=8.0 Hz, 1H), 7.34 (d, J=8.0 Hz, 1H), 7.19 (s, 1H), 7.08 (dd, J=8.0 Hz, J=8.0 Hz, 1H), 6.98 (dd, J=8.0 Hz, J=8.0 Hz, 1H), 3.50 (s, 2H), 3.13 (m, 2H), 3.03-2.82 (m, 18H), 1.88 (m, 6H), 1.78 (m, 2H), 1.62 (m, 4H)

¹³C-NMR (125.76 Mhz, d6-DMSO): 170.94, 136.10, 127.17, 123.75, 120.92, 118.67, 118.26, 111.33, 108.97, 57.39, 57.07, 46.12, 46.12, 44.06, 43.89, 43.89, 36.52, 36.22, 32.78, 26.71, 23.79, 23.06, 22.65, 22.65, 22.45

Structure: 1H-indole-3-acetamide, N-(20-amino-4-hydroxy-4,8,12,17-tetraazeicos-1-yl)

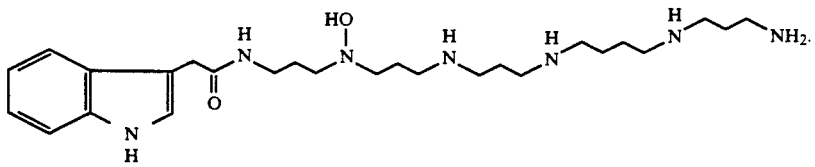

Alternatively and preferably, whole venom was fractionated as described in Example 1 except that the solvent system and linear gradient program used were 0%→20% B, 100%→80% A [0→30 min.] with peak detection at 220 nm. The fraction which eluted at about 26.0 minutes was loaded onto a Dynamax Phenyl column (4.6 mm×250 mm, 60 Å pore size, 8μ particle size) and eluted using a flow rate of 1 ml/min. and isocratic conditions of 10% B, 90% A where A and B are as described in Example 1. Peak detection was accomplished using a Waters 990 diode array detector (λ=220 nm) and fractions were collected as described in Example 1. The fraction which eluted at about 55.27 minutes was lyophilized from the eluent followed by lyophilization from water according to standard methods to yield the compound of this Example.

EXAMPLE 6

Subfractionation of Fraction G

Fraction G, obtained as described in Example 1, was loaded onto a C-18 Vydac ® (22 mm×250 mm, 300 Å pore size, 10μ particle size) column and eluted off using a flow rate of 10 ml/min. and a solvent system using a non-linear gradient program of 20%→30% B, 80%→70% A [0→40 min.] (Waters curve 6) and employing a Waters 990 diode array detector with fractions being collected as described in Example 1. Fraction G, after subfractionation as described above, eluted from the column at about 22 minutes. That fraction, which comprises a polypeptide, then was prepared for sequencing by lyophilization from the eluent followed by lyophilization from water, according to well known procedures.

Amino acid analysis of the alkylated polypeptide of the fraction was obtained using the Waters Pico-Tag method according to manufacturer's specifications. Sequence data was collected from an Applied Biosystems model 470A Protein/Peptide sequencer (Applied Biosystems, Inc., 850 Lincoln Center Drive, Foster City, Calif. 94404) with aqueous TFA conversion. Analysis of the resulting phenylthiohydantoin amino acids was accomplished on line with an Applied Biosystems model 120A PTH analyzer or off line on a DuPont Zorbax PTH column (Biomedical Product Department, Chromatography Products, E. I. duPont de Nemours and Co., Inc., 1007 Market Street, Wilmington, Del. 19898).

As a result of amino acid analysis and FAB MS of the entire polypeptide it was determined that the polypeptide comprised by fraction G is branched and the amino acid sequence was determined as:

$H_2N$—glu—lys—gly—leu—pro—glu—gly—ala—glu—cys—asp—gly —asn—glu—ser—asp—cys—lys—cys—ala—gly—gln—trp—ile—lys—cys—arg—cys—pro—trp—lys—trp—his—ile—thr—gly—glu—gly—pro—cys—thr—cys—glu—arg—gly—leu—lys—lys—thr—cys—ile—ser—lys—leu—ser—cys—pro—asn—arg—
                |
                SS—cys—pro—ser—$NH_2$ asn—glu—trp—COOH; and FAB MS: 7267.

EXAMPLE 7

Subfractionation of Fraction H and Determination of Structures Therein

Fraction H, obtained as described in Example 1, was loaded onto a C-18 Vydac ® (22 mm×250 mm, 300 Å pore size, 10μ particle size) column and eluted off using a flow rate of 10 ml/min. and a solvent system using a non-linear gradient program of 20%→25% B, 80%→75% A [0→30 min.] (Waters curve 6) then 25%→50% B, 75%→50% A [30→45 min.] (Waters curve 11), where A is 0.1% TFA and B is acetonitrile, and employing a Waters 990 diode array detector with fractions being collected as described in Example 1. Of the fractions collected, the fractions of interest were:

| Fraction | Elution Time |
| --- | --- |
| $H_1$ | about 29 minutes |
| $H_2$ | about 36 minutes |
| $H_3$ | about 41 minutes |

Fractions $H_1$, $H_2$ and $H_3$, which comprise polypeptides, then were prepared for sequencing and sequenced according to the procedures described in Example 6.

As a result of amino acid analysis and FAB MS it was determined that fraction $H_1$ comprises a polypeptide having the sequence:

$H_2N$—ala—cys—val—gly—glu—asn—gln—gln—cys—ala—asp—trp—ala—gly—pro—his—cys—cys—asp—gly—tyr—tyr—cys—thr—cys—arg—tyr—phe—pro—lys—cys—ile—cys—arg—asn—asn—asn—$CONH_2$ and FAB MS: 4198.

The polypeptide comprised by fraction $H_2$ was determined to be branched and to have an amino acid sequence of:

$H_2N$—ala—lys—ala—leu—pro—pro—gly—ser—val—cys—asp—gly—asn—glu—ser—asp—cys—lys—cys—try—gly—lys—trp—his—lys—cys—arg—cys—pro—trp—lys—trp—his—phe—thr—gly—glu—gly—pro—cys—thr—cys—glu—lys—gly—met—lys—his—thr—cys—ile—thr—lys—leu—his—
                |
                SS—cys—pro—ser—$NH_2$
cys—pro—asn—lys—ala—glu—trp—gly—leu—asp—trp—COOH; Ion-Spray MS: 7793.

EXAMPLE 8

Subfractionation of Fractions I and J and Determination of Structures Therein Fractions I and J, obtained as described in Example 1 and which were not adequately separated due to the similar elution times as shown in Example 1, were loaded together onto a C-4 Vydac ® (22 mm × 250 mm, 300 Å pore size, 10μ particle size) column and eluted off using a flow rate of 10 ml/min. and a solvent system using a non-linear gradient program of 20%→30% B, 80%→70% A [0→30 min.] (Waters curve 6), then 30%→50% B, 70%→50% A [30→45 min.] (Waters curve 11) where A is 0.1% aqueous TFA and B is acetonitrile. Peak detection and fraction collection were accomplished according to the procedures described in Example 6. Of the fractions collected, the fractions of interest were:

| Fraction | Elution Time |
|----------|--------------|
| I | about 22 minutes |
| J | about 27.5 minutes |

Fractions I and J, which comprise polypeptides, were prepared for sequencing and sequenced according to the procedures described in Example 6.

The amino acid sequence and FAB MS of the polypeptide comprised by fraction I were determined as:

H$_2$n—asp—cys—val—gly—glu—ser—gln—gln—
cys—ala—asp—trp—ala—gly—pro—his—cys—cys—
asp—gly—tyr—tyr—cys—thr—cys—arg—tyr—
phe—pro—lys—cys—ile—cys—val—asn—asn—asn—CONH$_2$ and
FAB MS: 4158.

The amino-terminal amino acid sequence of part of the polypeptide and FAB MS of the entire polypeptide comprised by fraction J was determined as:

H$_2$N—asp—glu—pro—cys—ile—pro—leu—gly—lys—
ser—cys—ser—trp—lys—ile—gly—thr—pro—tyr—
cys—cys—pro—his—pro—asp—asp—ala—gly—arg—
arg—thr—trp—cys—leu—val—asp—tyr—ser—arg—
phe—val—thr—ile—cys—ser—gly—arg—lys—tyr—CONH$_2$;
and FAB MS: 5506.

EXAMPLE 9

Determination of the Structure of Compound Comprised by Fraction K

Fraction K, obtained as described in Example 1 and which comprises a polypeptide, was prepared for sequencing and sequenced according to the procedures described in Example 6.

The amino acid sequence and FAB MS of the polypeptide comprised by fraction K were determined as:

H$_2$N—glu—asp—asn—cys—ile—ala—glu—asp—
tyr—gly—lys—cys—thr—trp—gly—gly—thr—lys—
cys—cys—arg—gly—arg—pro—cys—arg—cys—ser—
met—ile—gly—thr—asn—cys—glu—cys—thr—pro—
arg—leu—ile—met—glu—gly—leu—ser—phe—ala—COOH and
FAB MS 5274.

EXAMPLE 10

Subfractionation of Fraction L and Determination of Structures Therein

Fraction L, obtained as described in Example 1, was loaded onto a C-18 Vydac ® (10 mm × 250 mm, 300 Å pore size, 5μ particle size) column and eluted off using a flow rate of 3.5 ml/min. and a solvent system using a linear gradient program of 25%→40% B, 75%→60% A [0→30 min.] where A is 0.1% aqueous TFA and B is acetonitrile. Peak detection and fraction collection were accomplished according to the procedures described in Example 6. Of the fractions collected, the fractions of interest were:

| Fraction | Elution Time |
|----------|--------------|
| L$_1$ | about 20.25 minutes |
| L$_2$ | about 22.5 minutes |

Fractions L$_1$ and L$_2$, which comprise polypeptides, were prepared for sequencing and sequenced according to the procedures described in Example 6.

The amino-terminal amino acid sequence of part of the polypeptide comprised by fraction L$_1$ was determined as:

H$_2$N—ile—val—gly—gly—lys—thr—ala—lys—phe—
gly—asp—tyr—pro—trp—met—val—ser—ile—
gln—gln—lys—asn—lys—lys—gly—gly—phe—asp— and the molecular weight of the entire polypeptide was determined by gel electrophoresis according to known methods to be about 20,000.

EXAMPLE 11

Determination of Structure of Compound Comprising Fraction M

Fraction M, obtained as described in Example 1 and which comprises a polypeptide, was prepared for sequencing and sequenced according to the procedures described in Example 6.

The amino-terminal amino acid sequence of part of the polypeptide comprised by fraction M was determined as:

H$_2$N-glu-ala-thr-glu-ala-ala-lys-val-leu-ser-asn-leu-
asp-glu-thr-val-asp-proand the molecular weight of the entire polypeptide was determined by gel electrophoresis according to known methods to be about 80,000.

EXAMPLE 12

1H-Indole-3-acetamide,
N-(20-amino-4-hydroxy-4,8,12,17-tetraazeicos-1-yl

Synthesis of the title compound, ascertained to be comprised by fraction E as described in Example 4, was accomplished as described below.

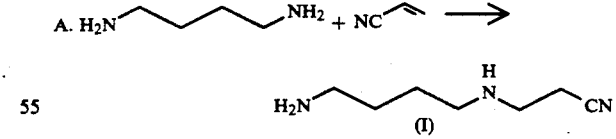

Under nitrogen atmosphere, 13.22 g (0.15 mole) diaminobutane and 3.5 ml methanol were stirred and 9.94 ml (0.15 mole) of acrylonitrile was added via a syringe pump over a two hour period with cooling to 0°–5° C. The mixture, after about 18 hours, was chromatographed on 600 g silica gel using a solvent system of 3:1 CH$_2$Cl$_2$/MeOH (2 liters) followed by 3:1 CH$_2$Cl$_2$/MeOH containing 5% by volume isopropylamine (2 liters). The fractions containing the coupled product were concentrated by evaporation in vacuo and yielded a yellow viscous oil. NMR analysis verified the product to be the coupled product of formula (I) shown above.

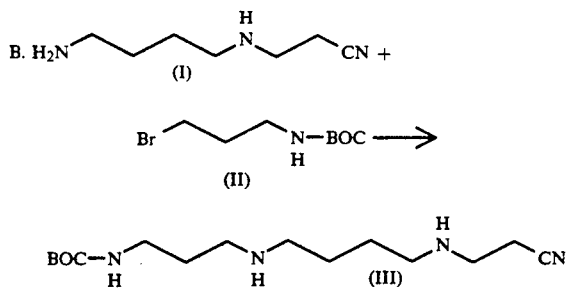

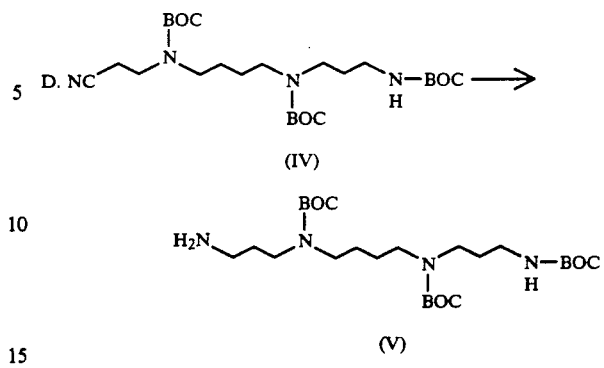

Under nitrogen atmosphere, 5.78 g (0.041 mole) of compound of formula I, prepared as described in part A above, was added to 75 ml of CH$_3$CN and 11.48 g of KF Celite and stirred. To the stirring mixture was added a solution of 9.75 g (0.041 mole) of compound of formula II, prepared according to the procedure described in Preparation A, in 25 ml of CH$_3$CN. The reaction was heated to reflux and monitored by TLC (3:1 CH$_2$Cl$_2$/MeOH). After three hours, the reaction was allowed to cool and stand at room temperature. The Celite was then filtered off and the filter-cake was washed well with dichloromethane. The filtrate was concentrated in vacuo. The crude product contained in the concentrated filtrate was chromatographed on silica gel using 2 liters of 3:1 CH$_2$Cl$_2$/MeOH, then 2 liters of 3:1 CH$_2$Cl$_2$/MeOH and 10 ml isopropylamine, then 2 liters of 3:1 CH$_2$Cl$_2$/MeOH and 30 ml isopropylamine. The product eluted from the column after the column became saturated with isopropylamine but was still impure. All product fractions were combined and concentrated. Silica gel was prepared by slurrying 500 g of silica gel in CH$_2$Cl$_2$ and 125 ml isopropylamine and then used to pack a column in the standard manner. The crude product was loaded onto the column using dichloromethane. Then, 500 ml of dichloromethane was run through the column, followed by one liter of 3:1 CH$_2$Cl$_2$/MeOH. The product fractions were combined and concentrated in vacuo to yield 1.5 g of product of formula III, above. Another 2 g of product of formula III was eluted off the column using one liter of 3:1 CH$_2$Cl$_2$/MeOH and 30 ml isopropylamine.

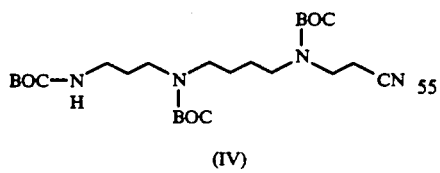

Under nitrogen atmosphere, 3.5 g (11.8 mmoles) of compound of formula III, prepared as described in part B, above, and 150 ml dichloromethane were stirred and 5.2 g (23.6 mmoles) of di-t-butyldicarbonate were added. The mixture was stirred for approximately 68 hours at room temperature. The mixture was then concentrated in vacuo and chromatographed using 400 g of silica gel and a 60:40 hexane/ethyl acetate solvent to yield 5.62 g of compound of formula IV as an oil.

Under nitrogen atmosphere, 3.0 g of compound of formula IV, prepared as described in part C, above, was dissolved in 30 ml of acetic acid in a 250 ml Parr ® bottle. To that solution was added 3.0 g of Pd(OH)$_2$/carbon and the mixture was hydrogenated at 50 p.s.i. H$_2$ pressure for 2 hours. The catalyst was removed by filtration and the cake was washed well with acetic acid. The filtrate was concentrated, taken up in 75 ml of dichloromethane, washed twice with 75 ml of 1N NaOH and dried over K$_2$CO$_3$. The solution was concentrated in vacuo to yield 2.86 g of product of formula V above.

E. V + NC↘ ⟶

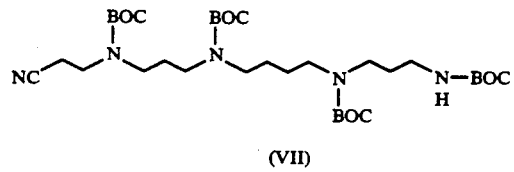

Under nitrogen atmosphere, 2.86 g (5.7 mmoles) of compound of formula V, prepared as described in part D, above, was dissolved in 75 ml methanol. With stirring, 0.41 ml (6.3 mmoles) of acrylonitrile was added to the mixture and the reaction was stirred overnight. The reaction mixture was then concentrated, reconcentrated three times from 30 ml dichloromethane and stripped of solvent in vacuo to yield 3.18 g of compound of formula VI as an oil.

F. VI ⟶

(VII)

Under nitrogen atmosphere, 3.18 g (5.7 mmoles) of compound of formula VI, prepared as described in part E, above, was combined with 100 ml of dichloromethane and stirred into solution. To that solution was added 1.37 g (6.3 mmoles) of di-t-butyldicarbonate and the reaction was stirred for 90 minutes at room temperature. The reaction mixture was then concentrated and chromatographed on 300 g silica gel using 60:40 hexane/ethyl acetate as the eluent. The product fractions were combined, concentrated, extracted with 3×20 ml dichloromethane and stripped of solvent in vacuo to yield 3.12 g of product of formula VII, above.

G. VII ⟶

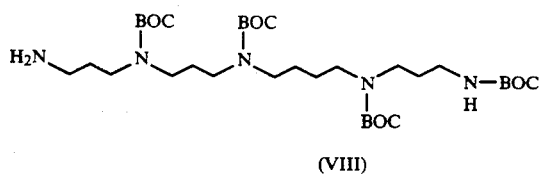

(VIII)

Following the procedure described in part D, above, 3.12 g (4.76 mmoles) of compound of formula VII, prepared as described in part F, above, was dissolved in 30 ml acetic acid and hydrogenated at 55 p.s.i. for 2 hours in the presence of 3.0 g Pd(OH)$_2$/carbon to yield 3.02 g of product of formula VIII, above, as an oil.

H. VIII + NC⟶ ⟶ 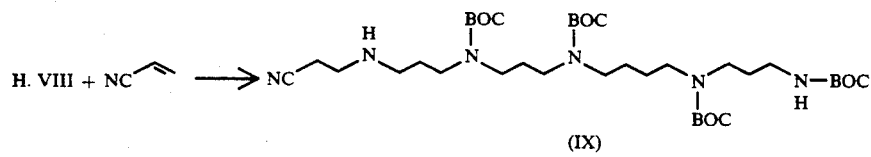

(IX)

Under nitrogen atmosphere, 1.0 g (1.5 mmoles) of compound of formula VIII, prepared as described in part G, was dissolved in 10 ml methanol. To that solution was added 0.1 ml (1.67 mmoles) of acrylonitrile and the reaction was stirred overnight. Then, the reaction mixture was concentrated, reconcentrated three times from 20 ml of dichloromethane and stripped of solvent in vacuo to yield 1.0 g of product of formula IX, above.

I. IX ⟶ 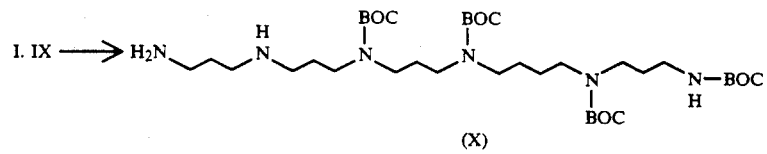

(X)

Following the procedure described in part D, above, 1.0 g (1.4 mmoles) of compound of formula IX, prepared as described in part H, above, was dissolved in 30 ml acetic acid and hydrogenated at 50 p.s.i. for 2.5 hours to yield 0.85 g of product of the formula X, above.

J.

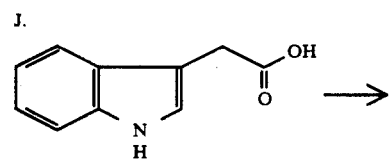

(XI)

A solution containing 6.78 g (20 mmoles) tetrabutylammonium hydrogen sulfate and 75 ml H$_2$O was prepared by stirring and 3.36 g (40 mmoles) of NaHCO$_3$ was added as foaming would allow. Then, 3.5 g (20 mmoles) of indole acetic acid was added, the mixture was stirred for 5 minutes and 75 ml of CHCl$_3$ was added. The mixture was stirred for another 5 minutes and the bottom two layers were separated. The aqueous layer was salted with Na$_2$SO$_4$ and extracted with CHCl$_3$. All CHCl$_3$ extracts were combined and dried over Na$_2$SO$_4$. The resulting clear amber colored solution was concentrated, chased with 3×75 ml acetone and finally dissolved in 75 ml acetone. Then, 1.9 ml (22 mmoles) of allyl bromide was added and the mixture was allowed to stand for 30 minutes. The mixture was then concentrated and chromatographed on silica gel using 3:1 hexane/ethyl acetate to yield 3.57 g of product of formula XI, above, as a light yellow oil.

K. XI ⟶ 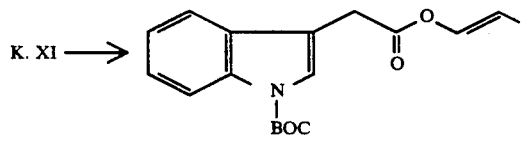

Following the procedure of Angew. Chem. Int. Ed. Engl. 23:298 (1984), 2.15 g (10 mmoles) of compound of formula XI, prepared as described in part J, above, was combined with 20 ml acetonitrile and 2.61 g (12 mmoles) of di-t-butyldicarbonate was added to the mixture. Then, 0.122 g (1 mmole) of 4-(N,N-dimethylamino)pyridine was added and the reaction permitted to proceed for 15 minutes. The mixture was then diluted out to 125 ml with ethyl acetate, washed 2×dilute HCl, 3×25 ml H$_2$O, 1×brine, dried and concentrated. The product was purified by chromatography on silica gel using 14.5:1 hexane/ethyl acetate as the eluent to yield 2.87 g of compound of the formula XII, above, as a colorless oil.

L. XII ⟶

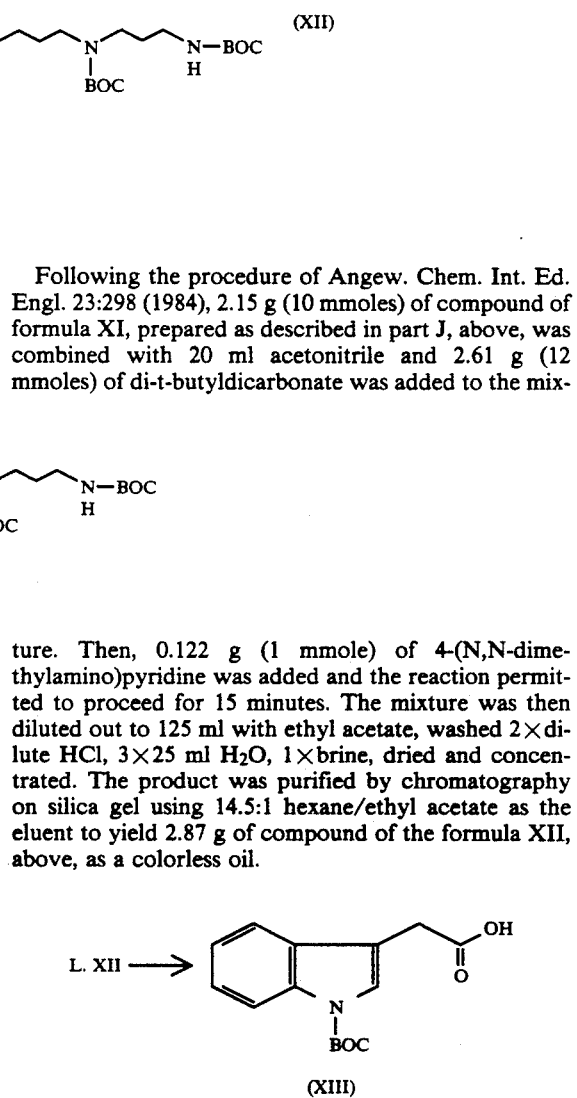

(XIII)

To 3.27 g (10.4 mmoles) of compound of formula XII, prepared according to part K, above, in 20 ml dichloromethane was added 7.4 ml of sodium 2-ethylhexanoate in ethyl acetate (0.231 g/ml). Then, 0.5 g φ$_3$P and 0.5 g ($\phi_3$P)$_4$Pd were added and the mixture was stirred for 60 minutes. The mixture was then concentrated, taken up in 150 ml ethyl acetate and washed 5×25 ml H$_2$O. The aqueous extracts were combined and back extracted with 1×25 ml ethyl acetate and 1×25 ml diethyl ether. To the aqueous layer was added 75 ml of fresh ethyl acetate and then acidified to pH 3. The ethyl acetate layer was separated and the aqueous layer was extracted with 1×50 ml fresh ethyl acetate. The two ethyl acetate extracts were combined and washed with 2×20 ml H$_2$O, then 1×20 ml brine, dried, concentrated, chased with 3×30 ml hexane where crystals formed during the second chase. The mixture was diluted out to 75 ml with hexane. The solids were filtered, washed well with hexane and air dried to yield 1.37 g of white solids. NMR confirmed the title structure of formula XIII.

chloroperoxybenzoic acid in 20 ml of acetone was added dropwise over 8-10 minutes. The reaction was stirred for 30 minutes then diluted out to 150 ml with diethylether and washed with 2×25 ml 10% K$_2$CO$_3$, 2×25 ml H$_2$O, 2×25 ml 10% , K$_2$CO$_3$, 2×25 ml H$_2$O and dried over K$_2$CO$_3$. The mixture was concentrated, chased with 2×30 ml dichloromethane and concentrated in vacuo to a steady weight of 0.33 g. NMR analysis showed the product to be a mixture of the desired product of formula XV, starting material and by-product. The product mixture was added to 3 ml of acetic acid to which was added 20 mg NaCNBH$_3$. The mixture was stirred overnight, stripped of acetic acid in vacuo, dissolved in 50 ml dichloromethane and washed 1×75 ml with aqueous buffer, pH 7. If necessary, the pH was adjusted to pH 7 with 1N NaOH and the dichloromethane layer was separated and washed with

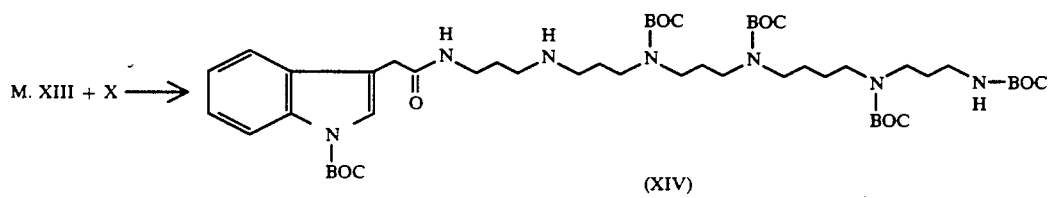

M. XIII + X ⟶

(XIV)

Under nitrogen atmosphere, 200 mg (0.73 mmoles) of the compound of formula XIII was combined with 25 ml dichloromethane, 84 mg (0.73 mmoles) N-hydroxysuccinimide and 150 mg (0.73 mmoles) dicyclohexylcarbodiimide whereupon a precipitate formed almost immediately. The mixture was stirred 3 hours. Then, the dicyclohexylurea was filtered off and to the filtrate was added dropwise a 40 ml solution of compound of the formula X, prepared as described in Example 12, Parts A-I in dichloromethane. The mixture was stirred for 12 hours then washed with 0.1 NaOH and dried over K$_2$CO$_3$, concentrated and chromatographed using 150 g silica gel and eluting with 9:1 dichloromethane/methanol (0.5 liters) to remove impurities then with 9:1:0.1 dichloromethane/methanol/isopropylamine (2 liters). The product was then concentrated, chased with dichloromethane and further concentrated to yield 400 mg of the compound of formula XIV, confirmed by 300 MHz NMR.

1×50 ml with aqueous buffer, pH 7 and 1×25 ml brine, dried over Na$_2$SO$_4$, and concentrated in vacuo to a steady weight of 0.31 g. The resulting product was chromatographed on 100 g silica gel using 95:5 ethyl acetate/methanol to elute and collecting 25 ml fractions. The purified product of formula XV came off in cuts 18-25. Those cuts were combined, concentrated, chased with 2×5 ml of dichloromethane and concentrated in vacuo to a white foam of 68 mg which was stored at −80° C. Cuts 26-40 which also contained the desired product also contained some impurity. Cuts 26-40 were combined, concentrated, chased with dichloromethane and concentrated in vacuo to a steady weight of 66 mg. The latter product was combined with 6 mg of the former product which had been used for NMR studies and with a mixture which had been prepared according to the procedure described above. The resulting mixture was chromatographed on 75 g silica gel using 9:5 ethyl acetate/methanol to elute and col-

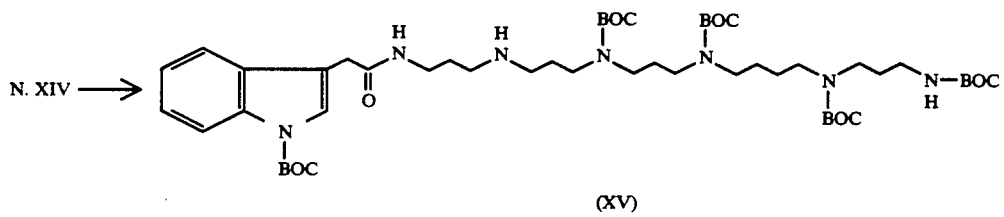

N. XIV ⟶

(XV)

Under nitrogen atmosphere, 0.34 g (0.35 mmoles) of the compound of formula XIV, prepared as described above, was combined with 30 ml acetone, stirred into solution and cooled to about 0° C. in an ice/acetone bath. Then, 0.212 g (1.05 mmoles) of 85% 3- lecting 25 ml fractions. Purified product of formula XV was present in cuts 16-21. Those cuts were combined, concentrated, chased with 2×5 ml dichloromethane and concentrated in vacuo to a steady weight of 46 mg which was stored at −80° C.

O. XV → 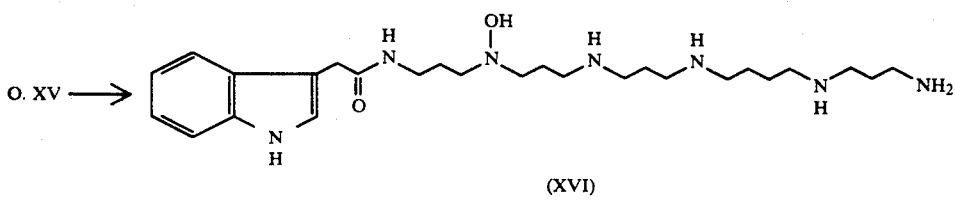

(XVI)

Under nitrogen atmosphere, 108 mg (0.109 mmoles) of compound of the formula XV, prepared as described above, was dissolved in 1.5 ml dichloromethane. Then, 2 ml of trifluoroacetic acid was added and the mixture was stirred for one hour at room temperature. The reaction mixture was then concentrated to a film and 15 ml diethylether was added. The film turned to solid and, after 30 minutes of stirring, yielded white powder. The powder was filtered, washed well with diethylether, dried under nitrogen, then evacuated to a steady weight of 109 mg of the title compound of this Example.

EXAMPLE 13

1H-Indole-3-acetamide, N-(20-amino-4-hydroxy-4,8,12,17-tetraazeicos-1-yl)-4-hydroxy Synthesis of the title compound, ascertained to be comprised by Fraction B₁ as described in Example 3, was accomplished as described below.

A. 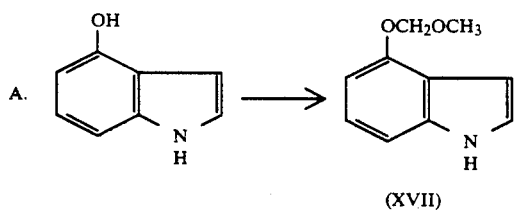

(XVII)

Under argon atmosphere using flame dried glassware, 4.0 g (30 mmoles) of 4-hydroxyindole was combined with 25 ml of Aldrich dry DMF and stirred into solution. Then, 1.44 g (30 mmoles) of NaH as a 50% oil dispersion was added. After foaming had subsided, 2.5 ml of chloromethylmethyl ether (Aldrich) was added and the resulting dark green solution was stirred overnight. Then, the solution was diluted to 125 ml with ethyl acetate, washed with 5×25 ml H₂O and 1×25 ml brine, dried over Na₂SO₄ and chromatographed using 4:1 hexane/ethyl acetate. The product containing fractions were combined and concentrated to yield 2.70 g of compound XVII as an oil.

B.

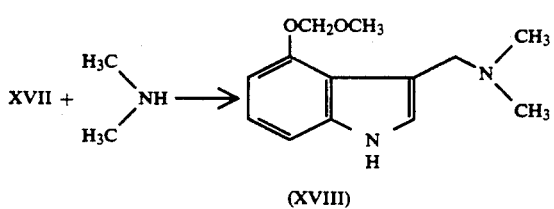

(XVIII)

In a 50 ml, 3 neck round bottom flask equipped with a mechanical stirrer and a nitrogen atmosphere was cooled 1.3 g of aqueous formaldehyde (37%) and 2.28 g of acetic acid. Then, 3.23 ml of cooled dimethylamine (25% in H₂O) was added. To the resulting cooled solution was added 2.7 g (15.2 mmoles) of compound of the formula XVII using about 1.5-2.0 ml of tetrahydrofuran as transfer solvent. The reaction was warmed to room temperature and stirred overnight. Then, 40 ml of 10% NaOH was added whereupon a precipitate formed. After stirring, the precipitate was filtered, washed with H₂O and air dried to yield 3.26 g of compound of the formula XVIII.

C. XVIII

↓

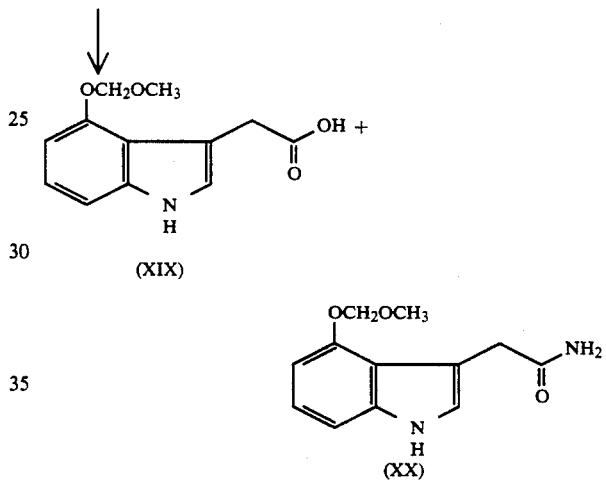

(XIX)

(XX)

Under nitrogen atmosphere, 4.62 g of KCN was combined with 10 ml H₂O and stirred into solution. Then 30 ml of ethanol and 3.26 g (14 mmoles) of compound XVIII were added and the mixture was stirred and heated to reflux for about 65 hours. The reaction was cooled and concentrated. The resulting precipitate comprising compound XX was filtered, washed with H₂O and air dried. The aqueous layer was extracted with 4×15 ml dichloromethane, saving the organic extracts. The aqueous layer then was overlayed with 50 ml ethyl acetate and acidified to pH 2. The ethyl acetate layer was separated, degassed by bubbling nitrogen through the ethyl acetate layer, dried and concentrated to a solid which was triturated with diisopropyl ether to yield 1.03 g of compound XIX as an off-white solid. Then, all extracts from the basic aqueous layer were combined, dried, combined with the filtrates from above and concentrated to yield 0.4 g of compound XX as a solid.

D.

XX→XIX

Under nitrogen atmosphere, 1.6 g of compound XX was combined with 7.5 ml of ethanol, 30 ml H₂O and 1.3 g KOH. The mixture was heated to reflux and stirred overnight. Then, the reaction was cooled, extracted with 2×15 ml ethyl acetate, overlayed with fresh ethyl acetate and acidified to pH 2. The combined ethyl acetate layers were dried and concentrated. The resulting solid was triturated with IPE to yield 1.1 g of compound XIX.

E.

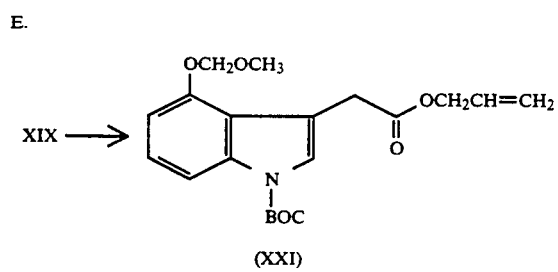

(XXI)

In 10 ml H₂O was dissolved 1.44 g (4.25 mmoles) TBAHSO₄. Then, 714 mg (8.5 mmoles) of NaHCO₃ was added. After foaming subsided, 1.0 g (4.25 mmoles) of compound of formula XIX was added and the mixture was stirred for one minute before 40 ml of chloroform was added. The reaction was stirred for 5 minutes, the chloroform layer was separated and then the aqueous mixture was extracted with 1×15 ml chloroform. The combined chloroform extracts were dried, concentrated and chased with 2×30 ml of acetone. Then, the product was redissolved in 30 ml of acetone under nitrogen atmosphere, 0.37 ml (4.25 mmoles) of allyl bromide was added and the reaction was stirred for 2 hours. The mixture was concentrated and chromatographed using ethyl acetate as the eluent. The product was concentrated to yield 1.1 g of an oil. All of the product was combined with 25 ml dichloromethane and 0.98 g (4.5 mmoles) of di-t-butyldicarbonate and 51 mg (0.425 mmoles) 4-(N,N-dimethylamino)pyridine were added. The reaction was stirred overnight. Then, the reaction mixture was concentrated and chromatographed using 9:1 hexane/ethyl acetate to yield, after concentration, 1.33 g of the compound of formula XXI as a viscous oil.

F.

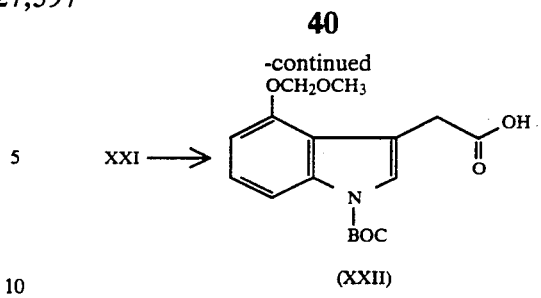

(XXII)

In 2 ml of methanol was dissolved 64 mg (0.17 mmoles) of compound of the formula XXI. To that solution was added 1.7 ml of 0.1 NaOH and the resulting reaction mixture was stirred overnight. The reaction then was acidified, dried, extracted with ethyl acetate and concentrated. NMR analysis showed all of the allyl ester of compound XXI had been removed but some trans esterification had occurred and some methyl ester was present. Therefore, the product was combined with the remaining amount of compound XXI (approx. 1.26 g), dissolved in 5 ml of tetrahydrofuran and cooled to 0° C. Then, 3.8 ml of 1N NaOH was added, the reaction was stirred for 5 minutes at 0° C. then allowed to warm to room temperature. The reaction resulted in two phases which required the addition of 5 ml methanol to eliminate the phases. The reaction was stirred overnight. Then, the tetrahydrofuran and methanol were stripped off and the remaining aqueous solution was overlayed with 50 ml ethyl acetate and acidified to pH 2. The ethyl acetate layer was separated, washed with 1×20 ml H₂O, once with brine, dried with Na₂SO₄, filtered and concentrated to a gum which crystallized when triturated with hexane to yield 1.08 g of white solid. The solid was chromatographed using 70:30 ethyl acetate/hexane and the clean product cuts were combined, concentrated and crystallized from ethyl acetate/hexane to yield 0.884 g of compound of the formula XXII.

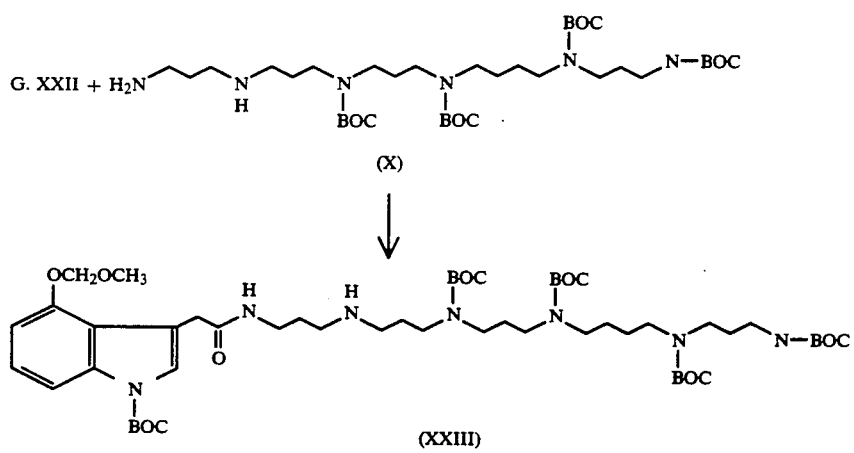

Under nitrogen atmosphere, 271 mg (0.81 mmoles) of compound of the formula XXII was dissolved with stirring in 4 ml of anhydrous tetrahydrofuran. Then, 93 mg (0.81 mmoles) of N-hydroxysuccinimide and 167 mg (0.81 mmoles) of dicyclohexylcarbodiimide were added and the mixture was stirred. After one hour and fifty minutes, 0.58 g (0.8 mmoles) of compound of the formula X, prepared according to the procedure described in Example 12, in 30 ml dichloromethane was added and the mixture stirred over the weekend. Then, the dicyclohexylurea was filtered off, and the mixture was extracted with 2×3 ml 1N NaOH, dried over K$_2$CO$_3$ and concentrated. The product then was chromatographed on 100 g silica gel using 9:1 dichloromethane/methanol to elute everything but the desired product then with 90:10:1 dichloromethane/methanol/isopropylamine to elute the product. The product containing fractions were concentrated, chased several times with dichloromethane and stripped of solvent to yield 349 mg of compound of the formula XXIII as a white foam.

Alternatively, and preferably, a 50 ml solution containing 0.480 g (1.43 mmoles) of compound of the formula XXII in dichloromethane was treated with 0.165 g (1.43 mmoles) of N-hydroxysuccinimide followed by 0.294 g (1.43 mmoles) of dicyclohexylcarbodiimide and allowed to stir for 5 hours. The reaction mixture was filtered and the filtrate containing crude hydroxysuccinimide was added dropwise over a 20 minute period to a 100 ml solution of 1.03 g (1.43 mmoles) of compound of the formula X, prepared according to the procedure described in Example 12, in dichloromethane. The reaction was stirred for 72 hours. Then, the crude reaction mixture was washed twice with 20 ml of 1N NaOH, dried over K$_2$CO$_3$, filtered and concentrated. The product was then chromatographed on silica gel using 4:1 dichloromethane/methanol followed by 9:1:1 dichloromethane/methanol/diisopropylamine to afford 912 mg of compound of the formula XXIII.

gassed. Then, the flask was wrapped in aluminum foil and 98 mg of compound XXIV was added with the use of about 2.5 ml dichloromethane as a transferring agent. After 45 minutes, the mixture was concentrated to yield an oil which, upon trituration with diethyl ether, yielded 88 mg of compound XXV as a white solid which was stored at −80° C.

Alternatively, and preferably, to a saturated 100 ml dioxane-HCl solution, purged with argon, was added, over 1.5 minutes, 0.520 g (0.495 mmoles) of compound of formula XXIV, prepared according to the procedure described in part H, above, in 10 ml of dioxane. A precipitate formed immediately and the reaction was stirred for 1 hour. Then, diethylether was added and, after 5 minutes, the solution was filtered. The resultant solids were washed with diethylether, dried under nitrogen atmosphere and then under reduced pressure to afford 345 mg of the acid of formula XXIV' which could be stored at −78° C. Then, to an aqueous solution, purged with argon, was added 150 mg (0.205 mmoles) of the acid of formula XXIV'. The reaction was monitored by HPLC. Upon completion of the reaction after about 7 hours, the reaction mixture was freeze dried to afford 103 mg of compound of the formula XXV as its hydrochloride salt.

EXAMPLE 14

Benzamide,

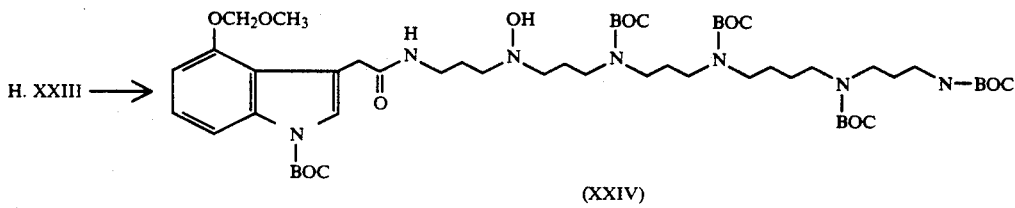

(XXIV)

Under a nitrogen atmosphere, indoleacetamide XXIII (900 mg, 0.87 mmol) was dissolved in 40 ml of dichloromethane. To this solution was added 2-(phenylsolfonyl)-3-phenyloxaziridine (500 mg, 1.92 mmol). Progress of the reaction was monitored by thin layer chromatography. After 1 hour the reaction mixture was concentrated in vacuo to give predominantly crude nitrone which was dissolved in 35 ml of acetic acid. A large excess of sodium cyanoborohydride (1.00 g, 15.9 mmol) was added and the reaction was allowed to stir for about 2 hours. The reaction was concentrated in vacuo, taken up in dichloromethane (50 ml), washed with pH 7 buffer (1×50 ml) adjusting the pH to 7 with 1N NaOH. The organic layer was washed again with pH 7 buffer (1×50 ml), dried over potassium carbonate, and concentrated in vacuo to generate crude product which was chromatographed on silica gel using 95:5 ethyl acetate/methanol to afford 612 mg (67%) of XXIV as a white foam.

N-(20-amino-4-hydroxy-4,8,12,17-tetraazeicos-1-yl)-4-hydroxy

Synthesis of the title compound, ascertained to be comprised by fraction A' as described in Example 2 was accomplished as described below.

A.

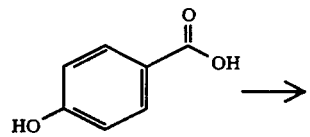

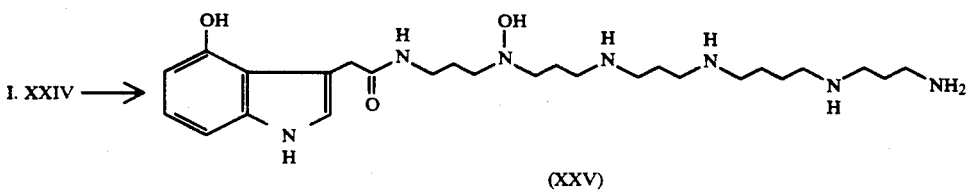

(XXV)

By alternately pulling a vacuum and bleeding with argon three times, 3 ml of trifluoroacetic acid was de- -continued

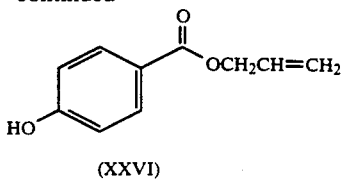

(XXVI)

In a 400 ml beaker, 6.78 g (20 mmoles) of tetrabutylammonium hydrogen sulfate was combined with 60 ml H$_2$O and stirred into solution. Then, 3.36 g (40 mmoles) of NaHCO$_3$ was added as foaming would allow followed by the addition of 40 ml of a solution containing 2.76 g (20 mmoles) p-hydroxybenzoic acid, 0.8 g NaOH and 40 ml H$_2$O. The reaction mixture was stirred for 5 minutes and then 200 ml of dichloromethane was added. The mixture was stirred for another 5 minutes and the layers were allowed to separate. The aqueous layer was extracted twice with 50 ml of dichloromethane. The combined dichloromethane extracts were dried over Na$_2$SO$_4$, concentrated, chased twice with 75 ml acetone and redissolved in 50 ml acetone. Then, 1.9 ml (22 mmoles) of allyl bromide were added and the mixture was stirred. The reaction mixture was then concentrated, taken up in 100 ml ethylacetate, washed twice with 30 ml H$_2$O, once with 50 ml saturated bicarbonate, once with 30 ml H$_2$O, once with brine, once with H$_2$O and once with brine. The resulting product was dried and concentrated to yield an oil. The oil was triturated with 50 ml petroleum ether for one hour. Then, the mixture was filtered, washed well with petroleum ether and air dried to yield 1.7 g of compound of the formula XXVI, above.

B.

XXVI ⟶ 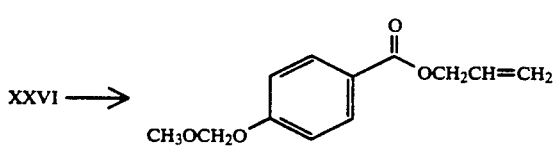

Under a nitrogen atmosphere, 1.7 g (9.55 mmoles) of compound of the formula XXVI, prepared as described in part A, above, was combined with 50 ml of Aldrich dry DMF and stirred into solution. Then, 0.38 g (9.55 mmoles) of NaH as a 60% oil dispersion was added and the reaction was stirred overnight. Then, 0.76 ml of chloromethylmethyl ether (Aldrich) was added whereupon a precipitate formed immediately. The reaction mixture was stirred for 18 hours. The reaction was quenched in 200 ml ethylacetate/100 ml H$_2$O. The ethylacetate layer was separated, washed 3 times with 50 ml HO, once with 50 ml 1N NaOH, once with 50 ml H$_2$O and once with brine. The resulting solution was dried, concentrated and chromatographed on silica gel using 4:1 hexane/ethylacetate to yield 1.63 g of compound of the formula XXVII, above.

C.

XXVII ⟶ 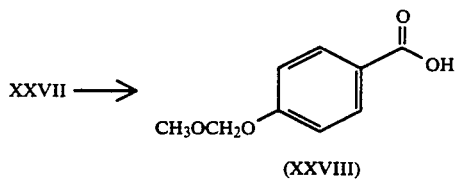

(XXVIII)

In 75 ml tetrahydrofuran was dissolved 1.62 g (7.3 mmoles) of compound of the formula XXVII, prepared as described in part B, above. Then a solution containing 0.4 g (10 mmoles) of NaOH in 15 ml of H$_2$O was added resulting in the formation of two layers. Methanol was added until a homogeneous mixture was obtained. The reaction was then stirred overnight. The tetrahydrofuran and methanol were stripped off in vacuo and the remaining aqueous solution was extracted twice with 15 ml ethylacetate. Then, the aqueous layer was overlayed with 50 ml of fresh ethylacetate and acidified to pH 2.5 with 6N HCl. Then ethylacetate layer was separated, washed once with 10 ml H$_2$O and once with 25 ml brine. The resulting solution was concentrated to yield solids which were triturated with hexane, filtered and air dried to yield 1.2 g of compound of formula XXVIII, above.

D. X + XXVIII ⟶ 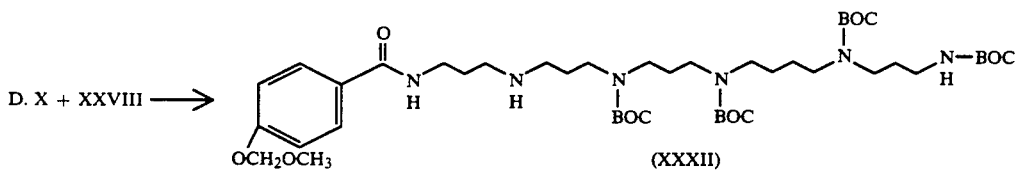

(XXXII)

A 20 ml dichloromethane solution containing 0.127 g (0.7 mmoles) of compound of the formula XXVIII, prepared as described in Part C, above, was treated with 0.081 g (0.7 mmoles) of N-hydroxysuccinimide followed by 0.144 g (0.7 mmoles) of dicyclohexylcarbodiimide and allowed to stir for 4 hours. Then, the reaction mixture was filtered and the filtrate containing crude hydroxysuccinimide was added dropwise over a 20 minute period to a 80 ml dichloromethane solution containing 0.50 g (0.7 mmoles) of compound of the formula X, prepared according to the procedure described in Example 12, Parts A-I, above. The reaction was then stirred for 17 hours. The reaction mixture was then washed with 1N NaOH (2×20 ml), dried over potassium carbonate, filtered and concentrated. The concentrate was chromatographed on silica gel using 9:1 dichloromethane/methanol followed by 9:1:0.25 dichloromethane/methanol/diisopropylamine to yield 370 mg of compound of the formula XXXII, above.

E. XXXII ⟶ 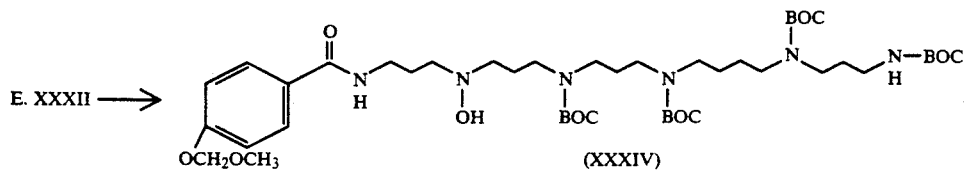

(XXXIV)

Under a nitrogen atmosphere, 0.335 g (0.38 mmoles) of compound of the formula XXXII, prepared according to the procedure described in Part D, above, was dissolved in 30 ml of dichloromethane. To this solution was added 0.230 g (0.88 mmoles) of 2-(sulfonylphenyl)-3-phenyl-oxaziridine. After 0.5 hour the reaction was concentrated in vacuo and the concentrate was dissolved in 15 ml of acetic acid. A large excess of cyanoborohydride (0.100 g, 1.6 mmoles) was added and the reaction was stirred for 2 hours. Then, the reaction was concentrated in vacuo, taken up in 50 ml of dichloromethane, washed once with 50 ml of pH 7 buffer, adjusting the pH to 7 with 1N NaOH. The organic layer was washed again with 50 ml of pH 7 buffer, dried over potassium carbonate and concentrated in vacuo. The concentrate was chromatographed on silica gel using 50:50 acetone/hexane to yield 253 mg of compound of the formula XXXIV, above.

F. (XXXIV) ⟶ 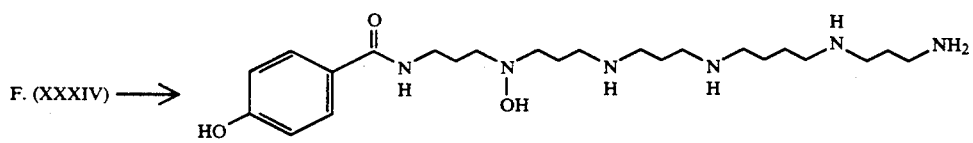

Under an argon atmosphere at room temperature were combined 0.20 g (0.223 mmoles) of compound of the formula XXXIV, prepared according to the procedure described in Part E, above, and 5 ml of trifluoroacetic acid. The reaction was stirred for 1.5 hours. An additional 2 ml of trifluoroacetic acid was added to wash the walls of the flask. The reaction was allowed to proceed for an additional 1.5 hours. Then, the reaction was concentrated in vacuo, triturated with ethyl ether, filtered and dried under a nitrogen atmosphere to afford 218 mg of compound of the formula XXXVI, the title compound of this Example.

EXAMPLE 15

Benzamide, N-(20-amino-4-hydroxy-4,8,12,17-tetraazeicos-1-yl)-2,5-dihydroxy

Synthesis of the title compound, ascertained to be comprised by fraction $A_1$ as described in Example 3, was accomplished as described below.

A.

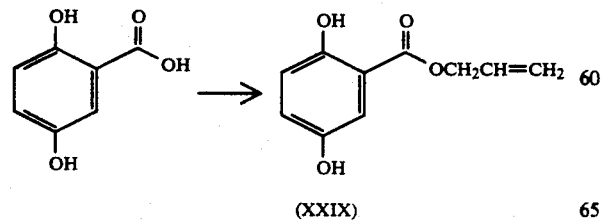

(XXIX)

Employing the procedure described in Example 13, Part A, but starting with 3.08 g (20 mmoles) of 2,5-dihydroxybenzoic acid yielded 3.0 g of compound of the formula XXIX, above.

B.

XXIX ⟶ 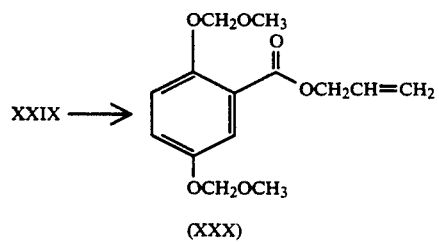

(XXX)

Under nitrogen atmosphere, 3.0 g (15.5 mmoles) of compound of the formula XXIX was combined with 50 ml of Aldrich dry DMF and stirred into solution. Then, 1.24 g (31 mmoles) of NaH as a 60% oil dispersion was added and the mixture was stirred. After 3 hours, 2.5 ml (33 mmoles) of chloromethylmethyl ether was added and the reaction was stirred for 18 hours. The reaction mixture was then added to 300 ml ethylacetate and 100 ml H$_2$O. The ethylacetate layer was then separated and washed 3 times with 75 ml H$_2$O, twice with 75 ml 1N NaOH, twice with 50 ml H$_2$O and once with brine. The resulting solution was dried and concentrated to yield 2.9 g of an oil which was chromatographed on silica gel using 4:1 hexane/ethylacetate to yield two fractions, the second fraction of which contained 1.16 g of compound of the formula XXX, above.

C.

XXX ⟶ 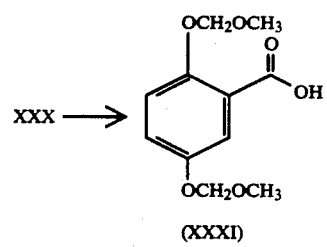

(XXXI)

To 10 ml of tetrahydrofuran was added 1.16 g (4.1 mmoles) of compound of the formula XXX, above. Then, 0.24 g (6 mmoles) of NaOH in 10 ml H$_2$O was added which resulted in the formation of two phases. Methanol was added to the mixture until one phase was obtained and then the mixture was stirred for 18 hours. The solvents were then removed and the remaining aqueous solution was extracted twice with 15 ml of ethylacetate. The aqueous layer was then overlayed with 35 ml of fresh ethylacetate and the pH was adjusted to 2.5 with 6N HCl. The ethylacetate layer was then separated, washed once with 10 ml H₂O, and once with brine, dried and concentrated to yield 1.0 g of compound of the formula XXXI, above, as an oil.

EXAMPLE 16

1H-Indole-3-acetamide, N-(16-amino-4-hydroxy-4,8,13-triazahexadec-1-yl)-4-hydroxy Synthesis of the title compound, ascertained to be comprised by fraction $A_2$ as described in Example 3,

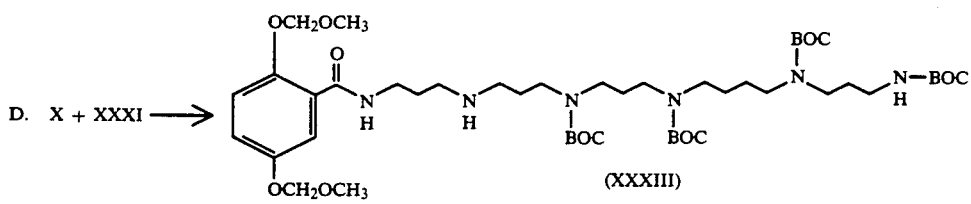

Employing the procedure described in Example 14, Part D, and using 0.17 g (0.7 mmoles) of compound of the formula XXXI, prepared as described in Part C, above, 0.081 g (0.7 mmoles) N-hydroxysuccinimide, 0.144 g (0.7 mmoles) dicyclohexylcarbodiimide and 0.50 g (0.7 mmoles) of compound of the formula X, prepared according to the procedure described in Example 12, Parts A–I, yielded, after chromatography, 370 mg of compound of the formula XXXIII, above.

was accomplished as described below.

A. VI ⟶

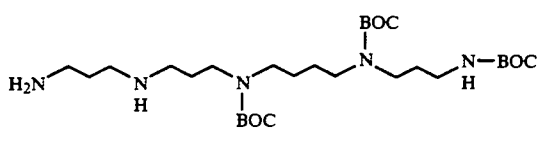

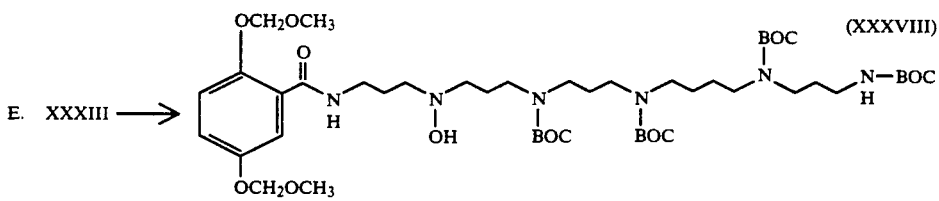

Employing the procedure described in Example 14, Part E, and using 0.308 g (0.33 mmoles) of compound of the formula XXXIII, prepared according to the procedure described in Part D, above, and 0.250 g (0.96 mmoles) of 2-(sulfonylphenyl)-3-phenyl-oxaziridine yielded, after silica gel chromatography using ethylacetate followed by 50:50 acetone/hexane, 210 mg of compound of the formula XXXV, above.

Employing the procedure described in Example 12, Part D, and using 1.15 g (2.07 mmoles) of compound of the formula VI, prepared as described in Example 12, Parts A–E, yielded 1.10 g of crude compound of the formula XXXVIII, above.

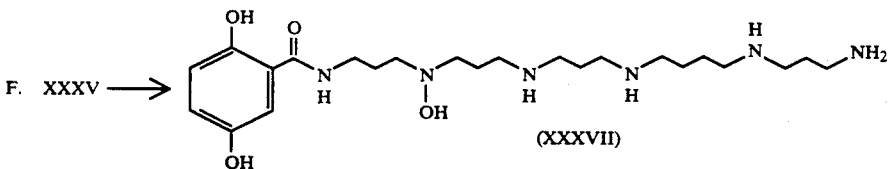

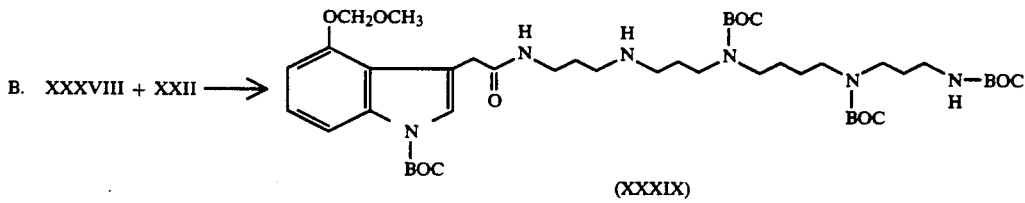

Employing the procedure described in Example 14, Part F, and using 0.100 g (0.104 mmoles) of compound of the formula XXXV, prepared according to the procedure described in Part E, above, yielded 108 mg of compound of the formula XXXVII, the title compound of this Example.

Employing the alternate procedure described in Example 13, Part G, and using a dichloromethane solution (15 ml) containing 0.228 g (6.8 mmoles) of compound of the formula XXII, prepared as described in Example 13, Parts A to F, above, 0.380 g (6.8 mmoles) of compound of the formula XXXVIII, prepared as described in Part A, above, 0.078 g (6.8 mmoles) of N-hydroxysuccinimide and 0.140 g (6.8 mmoles) of dicyclohexylcarbodiimide afforded 0.407 g of compound of the formula XXXIX after silica gel chromatography using 9:1 dichloromethane/methanol followed by 9:1:05 dichloromethane/methanol/diisopropylamine.

32.3 ml (236 mmoles) triethylamine. A precipitate formed immediately. The reaction was stirred overnight. The reaction mixture was then diluted to 1.5 liters with ethylacetate, washed once with 500 ml of 1N HCl, three times with 500 ml water, once with brine and dried over $Na_2SO_4$. After concentration, the product was chromatographed on 800 g silica gel using 4:1 hex- C. XXXIX ⟶ 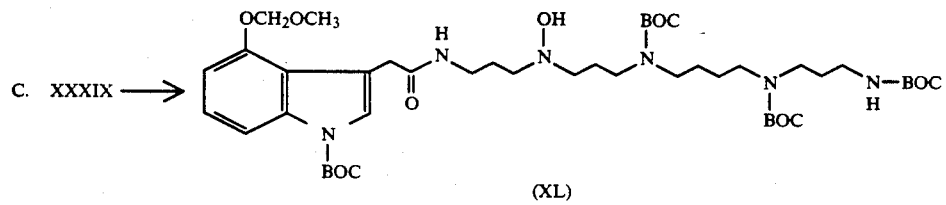

(XL)

Employing the procedure described in Example 13, Part H, and using 0.350 g (0.4 mmoles) of compound of the formula XXXIX and 0.230 g (0.88 mmoles) of 2-(sulfonylphenyl)-3-phenyloxziridine gave 0.274 g of compound of the formula XL, above, after silica gel chromatography using 50:50 acetone/hexane. The product contained a minor amount of phenylsulfonamide and therefore was further purified on silica gel using ethylacetate followed by 50:50 acetone/hexane.

ane/ethylacetate and the fractions were monitored by thin layer chromatography ($KMNO_4/I_2$). The fractions containing the product were combined, concentrated in vacuo, chased twice with 50 ml dichloromethane and purged with high vacuum to yield 25.8 g of the product of this Preparation.

What is claimed is:

1. A substantially pure compound of the formula

D. XL ⟶ 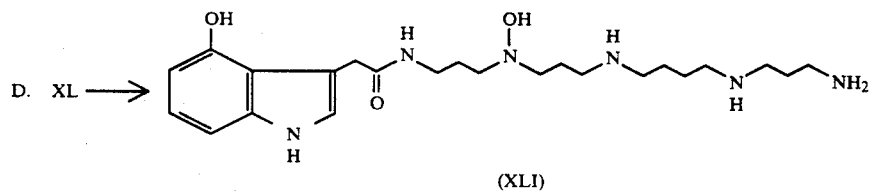

(XLI)

Employing the alternate procedure of Example 13, Part I, and using 0.166 g (0.186 mmoles) of compound of the formula XL, prepared according to the procedure described in Part C, above, provided after dioxane/HCl treatment crude acid. The acid of formula XL' was dissolved in water for 8 hours, followed by freeze drying to yield 88 mg of compound of the formula XLI.

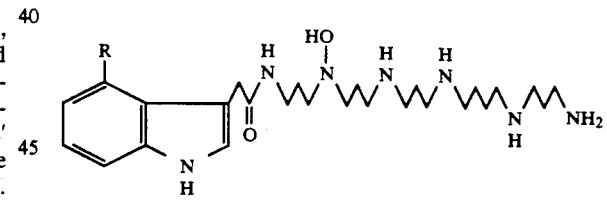

and the pharmaceutically-acceptable salts thereof, wherein R is H or OH.

2. The compound or a pharmaceutically-acceptable salt thereof according to claim 1 wherein R is H.

3. The compound or a pharmaceutically-acceptable salt thereof according to claim 1 wherein R is OH.

4. A substantially pure compound of the formula

PREPARATION A

Br⁀⁀N—BOC
           H

Under nitrogen atmosphere, 34.5 g (157.6 mmoles) of 3-bromopropylamine·HBr in 600 ml of N,N-dimethylformamide was stirred. To that solution was added 34.4 g (157.6 mmoles) of di-t-butyldicarbonate followed by

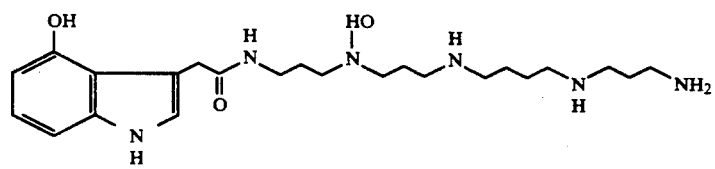

and the pharmaceutically-acceptable salts thereof.

5. A substantially pure compound of the formula

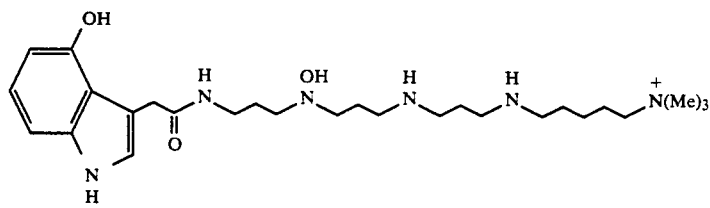

and the pharmaceutically-acceptable salts thereof.

6. A method of blocking calcium channels in a cell which comprises administering to said cell a calcium channel blocking amount of a compound according to claim 1 wherein R is OH or a pharmaceutically-acceptable salt thereof.

7. The method according to claim 6 wherein the cell is in the nervous system of a mammal.

8. The method according to claim 6 wherein the cell is in the nervous system of an invertebrate.

9. A method of antagonizing excitatory amino acid neurotransmitters which neurotransmitters affect a cell, said method comprising administering to said cell an excitatory amino acid neurotransmitter antagonizing amount of a compound according to claim 1 or a pharmaceutically-acceptable salt thereof.

10. The method according to claim 9 wherein the cell is in the nervous system of a mammal.

11. The method according to claim 9 wherein the cell is in the nervous system of an invertebrate.

12. A method of antagonizing excitatory amino acid neurotransmitters which affect a cell and blocking calcium channels in a cell which comprises administering an excitatory amino acid neurotransmitter antagonizing and calcium channel blocking amount of a compound according to claim 1 wherein R is OH or a pharmaceutically-acceptable salt thereof.

13. The method according to claim 12 wherein the cell is in the nervous system of a mammal.

14. The method according to claim 12 wherein the cell is in the nervous system of an invertebrate.

15. A method of antagonizing excitatory amino acid neurotransmitters which neurotransmitters affect a cell, said method comprising administering to said cell an excitatory amino acid neurotransmitter antagonizing amount of a compound according to claim 4 or a pharmaceutically-acceptable salt thereof.

16. The method according to claim 15 wherein the cell is in the nervous system of a mammal.

17. The method according to claim 15 wherein the cell is in the nervous system of an invertebrate.

18. The method according to claim 6 wherein the cell is a muscle cell in a mammal.

19. The method according to claim 6 wherein the cell is a muscle cell in an invertebrate.

20. A method of antagonizing excitatory amino acid neurotransmitters which affect a neuronal cell and blocking calcium channels in a neuronal cell and calcium channels in a muscle cell, said method comprising administering to said cells an excitatory amino acid neurotransmitter antagonizing and calcium channel blocking amount of a compound according to claim 1 wherein R is OH or a pharmaceutically-acceptable salt thereof.

21. The method according to claim 20 wherein the cells are in a mammal.

22. The method according to claim 21 wherein the cells are in an invertebrate.

23. A pharmaceutical composition for blocking calcium channels in a cell in the nervous system of a mammal which comprises a calcium channel blocking amount of a compound according to claim 1 wherein R is OH or a pharmaceutically-acceptable salt thereof and a pharmaceutically-acceptable diluent or carrier.

24. A pharmaceutical composition for antagonizing excitatory amino acid neurotransmitters which affect a cell in the nervous system of a mammal, said composition comprising an excitatory amino acid neurotransmitter antagonizing amount of a compound according to claim 1 or a pharmaceutically-acceptable salt thereof and a pharmaceutically-acceptable diluent or carrier.

25. A pharmaceutical composition for antagonizing excitatory amino acid neurotransmitters which affect a cell in the nervous system of a mammal and blocking calcium channels in a cell in the nervous system of a mammal, said composition comprising an excitatory amino acid neurotransmitter antagonizing and calcium channel blocking amount of a compound according to claim 1 wherein R is OH or a pharmaceutically-acceptable salt thereof and a pharmaceutically-acceptable diluent or carrier.

26. A pharmaceutical composition for antagonizing excitatory amino acid neurotransmitters which affect a cell in the nervous system of a mammal, said composition comprising an excitatory amino acid neurotransmitter antagonizing amount of a compound according to claim 4 or a pharmaceutically-acceptable salt thereof and a pharmaceutically-acceptable diluent or carrier.

27. A pharmaceutical composition for antagonizing excitatory amino acid neurotransmitters which affect a cell in the nervous system of a mammal, said composition comprising an excitatory amino acid neurotransmitter antagonizing amount of a compound according to claim 5 or a pharmaceutically-acceptable salt thereof and a pharmaceutically-acceptable diluent or carrier.

28. A pharmaceutical composition for antagonizing excitatory amino acid neurotransmitters which affect a cell in the nervous system of a mammal and blocking calcium channels in a cell in the nervous system of a mammal, said composition comprising an excitatory amino acid neurotransmitter antagonizing and calcium channel blocking amount of a compound according to claim 1 wherein R is OH or a pharmaceutically-acceptable salt thereof and a pharmaceutically-acceptable diluent or carrier.

* * * * *